US012758406B2

(12) United States Patent
Gilmartin et al.

(10) Patent No.: US 12,758,406 B2
(45) Date of Patent: Oct. 13, 2026

(54) STENT WITH ANTI-MIGRATION FEATURE

(71) Applicant: BOSTON SCIENTIFIC SCIMED, INC., Maple Grove, MN (US)

(72) Inventors: Gary Gilmartin, Foxford (IE); Matthew Montague, Galway (IE); Louis McNern, Donegal (IE); Michael Walsh, Galway (IE); Geraldine Toner, Raphoe (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 875 days.

(21) Appl. No.: 18/145,548

(22) Filed: Dec. 22, 2022

(65) Prior Publication Data

US 2023/0132028 A1 Apr. 27, 2023

Related U.S. Application Data

(63) Continuation of application No. 16/735,215, filed on Jan. 6, 2020, now Pat. No. 11,559,412.

(60) Provisional application No. 62/789,391, filed on Jan. 7, 2019.

(51) Int. Cl.
*A61F 2/88* (2006.01)
*A61F 2/90* (2013.01)

(52) U.S. Cl.
CPC .................. *A61F 2/88* (2013.01); *A61F 2/90* (2013.01); *A61F 2210/0014* (2013.01); *A61F 2220/0008* (2013.01); *A61F 2240/001* (2013.01)

(58) Field of Classification Search
CPC ................. A61F 2/86; A61F 2/88; A61F 2/90
See application file for complete search history.

(56) References Cited

U.S. PATENT DOCUMENTS 3,938,529 A 2/1976 Gibbons
5,064,435 A 11/1991 Porter
5,133,732 A 7/1992 Wiktor
(Continued)

FOREIGN PATENT DOCUMENTS

CN 201108514 Y 9/2008
CN 201684049 U 12/2010
(Continued)

OTHER PUBLICATIONS

International Search Report and Written Opinion dated Mar. 19, 2020 for International Application No. PCTUS2020012373.

*Primary Examiner* — Leslie A Lopez
(74) *Attorney, Agent, or Firm* — Seager, Tufte & Wickhem, LLP

(57) ABSTRACT

An illustrative stent may comprise an elongated tubular member having a longitudinal axis, the elongated tubular member comprising at least one knitted filament forming a plurality of twisted knit stitches with intermediate rung portions extending circumferentially between radially adjacent twisted knit stitches. Each twisted knit stitch may be interconnected with a longitudinally adjacent twisted knit stitch forming a series of linked stitches. The elongated tubular member may be configured to move between a collapsed configuration and an expanded configuration, wherein in the collapsed configuration the series of linked stitches form longitudinal columns and in the expanded configuration the series of linked stitches extend helically around the elongated tubular member.

20 Claims, 30 Drawing Sheets

(56) References Cited

U.S. PATENT DOCUMENTS

| | | | | |
|---|---|---|---|---|
| 5,238,004 | A | 8/1993 | Sahatjian et al. | |
| 5,366,504 | A | 11/1994 | Andersen et al. | |
| 5,383,927 | A | 1/1995 | De Goicoechea et al. | |
| 5,607,464 | A | 3/1997 | Trescony et al. | |
| 5,628,788 | A | 5/1997 | Pinchuk | |
| 5,645,559 | A | 7/1997 | Hachtman et al. | |
| 5,653,745 | A | 8/1997 | Trescony et al. | |
| 5,662,713 | A * | 9/1997 | Andersen | A61F 2/958 128/898 |
| 5,697,970 | A | 12/1997 | Schmitt et al. | |
| 5,800,519 | A | 9/1998 | Sandock | |
| 5,876,445 | A * | 3/1999 | Andersen | A61L 31/04 623/23.7 |
| 5,984,965 | A | 11/1999 | Knapp et al. | |
| 6,161,399 | A * | 12/2000 | Jayaraman | D04C 1/06 66/170 |
| 6,221,060 | B1 | 4/2001 | Willard | |
| 6,240,978 | B1 | 6/2001 | Gianotti | |
| 6,258,117 | B1 | 7/2001 | Camrud et al. | |
| 6,264,689 | B1 | 7/2001 | Colgan et al. | |
| 6,305,436 | B1 | 10/2001 | Andersen et al. | |
| 6,358,275 | B1 | 3/2002 | Mollroy et al. | |
| 6,416,537 | B1 | 7/2002 | Martakos et al. | |
| 6,451,052 | B1 | 9/2002 | Burmeister et al. | |
| 6,485,515 | B2 | 11/2002 | Strecker | |
| 6,494,907 | B1 | 12/2002 | Bulver | |
| 6,508,803 | B1 | 1/2003 | Horikawa et al. | |
| 6,520,983 | B1 | 2/2003 | Colgan et al. | |
| 6,540,773 | B2 | 4/2003 | Dong | |
| 6,554,855 | B1 | 4/2003 | Dong | |
| 6,652,577 | B2 | 11/2003 | Gianotti | |
| 6,709,451 | B1 | 3/2004 | Noble et al. | |
| 6,783,554 | B2 | 8/2004 | Amara et al. | |
| 6,893,457 | B2 | 5/2005 | Dong | |
| 6,939,372 | B2 | 9/2005 | Dong | |
| 7,011,676 | B2 | 3/2006 | Dong | |
| 7,169,139 | B2 | 1/2007 | Teague et al. | |
| 7,195,646 | B2 | 3/2007 | Nahleili | |
| 7,198,638 | B2 | 4/2007 | Dong | |
| 7,338,530 | B2 | 3/2008 | Carter et al. | |
| 7,364,587 | B2 | 4/2008 | Dong et al. | |
| 7,594,928 | B2 | 9/2009 | Headley, Jr. et al. | |
| D612,499 | S | 3/2010 | Ondracek et al. | |
| 7,854,756 | B2 | 12/2010 | Shaw | |
| 8,435,283 | B2 | 5/2013 | Jordan et al. | |
| 8,435,285 | B2 | 5/2013 | Shank et al. | |
| 8,454,675 | B2 | 6/2013 | Houston et al. | |
| 8,753,407 | B2 | 6/2014 | Nguyen | |
| 8,974,516 | B2 | 3/2015 | Hyodoh et al. | |
| 9,265,635 | B2 | 2/2016 | Walak | |
| 9,498,319 | B2 | 11/2016 | Walak | |
| 9,839,508 | B2 | 12/2017 | Walsh et al. | |
| 9,849,009 | B2 | 12/2017 | Thompson | |
| 9,849,010 | B2 | 12/2017 | Thompson | |
| 2002/0179166 | A1 | 12/2002 | Houston et al. | |
| 2003/0040771 | A1 | 2/2003 | Hyodoh et al. | |
| 2003/0093145 | A1 | 5/2003 | Lawrence-Brown et al. | |
| 2003/0191517 | A1 | 10/2003 | Osborne et al. | |
| 2004/0039435 | A1 | 2/2004 | Hancock et al. | |
| 2004/0127973 | A1 | 7/2004 | Mangiardi et al. | |
| 2004/0167606 | A1 * | 8/2004 | Chouinard | A61F 2/90 623/1.53 |
| 2005/0033418 | A1 | 2/2005 | Banas et al. | |
| 2005/0049682 | A1 | 3/2005 | Leanna et al. | |
| 2005/0110214 | A1 * | 5/2005 | Shank | A61F 2/82 273/274 |
| 2005/0154448 | A1 | 7/2005 | Cully et al. | |
| 2005/0240261 | A1 | 10/2005 | Rakos et al. | |
| 2005/0240278 | A1 | 10/2005 | Aliski et al. | |
| 2006/0265051 | A1 | 11/2006 | Caro et al. | |
| 2007/0123969 | A1 | 5/2007 | Gianotti | |
| 2007/0282453 | A1 | 12/2007 | Weitzner et al. | |
| 2007/0299506 | A1 | 12/2007 | Carter et al. | |
| 2008/0103584 | A1 * | 5/2008 | Su | A61F 2/86 623/1.16 |
| 2008/0228262 | A1 | 9/2008 | Goldmann et al. | |
| 2009/0005855 | A1 * | 1/2009 | Goto | A61F 2/07 623/1.15 |
| 2009/0030363 | A1 | 1/2009 | Gellman | |
| 2009/0138070 | A1 * | 5/2009 | Holzer | A61F 2/07 623/1.42 |
| 2009/0187240 | A1 | 7/2009 | Clerc et al. | |
| 2009/0276029 | A1 | 11/2009 | Caro et al. | |
| 2010/0030321 | A1 | 2/2010 | Mach | |
| 2010/0100170 | A1 | 4/2010 | Tan et al. | |
| 2010/0256731 | A1 | 10/2010 | Mangiardi | |
| 2010/0256735 | A1 * | 10/2010 | Morales, Jr. | A61F 2/90 623/1.22 |
| 2011/0213453 | A1 | 9/2011 | Mangiardi | |
| 2012/0116528 | A1 | 5/2012 | Nguyen | |
| 2012/0165956 | A1 | 6/2012 | Li | |
| 2012/0290100 | A1 | 11/2012 | Li | |
| 2012/0296257 | A1 | 11/2012 | Van Dam et al. | |
| 2014/0243992 | A1 | 8/2014 | Walsh et al. | |
| 2014/0277560 | A1 | 9/2014 | Walak | |
| 2014/0277561 | A1 | 9/2014 | Jordan | |
| 2014/0343683 | A1 | 11/2014 | Jeon et al. | |
| 2015/0282955 | A1 | 10/2015 | Guler et al. | |
| 2016/0095724 | A1 | 4/2016 | Harris et al. | |

FOREIGN PATENT DOCUMENTS

| | | | |
|---|---|---|---|
| JP | 2009006033 | A | 1/2009 |
| JP | 2011160915 | A | 8/2011 |
| JP | 2016105790 | A | 6/2016 |
| WO | 2008076706 | A2 | 6/2008 |
| WO | 2014134352 | A1 | 9/2014 |
| WO | 2014164308 | A1 | 10/2014 |

* cited by examiner

STENT WITH ANTI-MIGRATION FEATURE

CROSS-REFERENCE TO RELATED APPLICATIONS

This application is a continuation of U.S. application Ser. No. 16/735,215, filed Jan. 6, 2020, which claims the benefit of priority of U.S. Provisional Application No. 62/789,391 filed Jan. 7, 2019, the entire disclosures of which are hereby incorporated by reference.

TECHNICAL FIELD

The present disclosure pertains to medical devices, methods for manufacturing medical devices, and uses thereof. More particularly, the present disclosure pertains to a stent for implantation in a body lumen, and associated methods.

BACKGROUND

Implantable medical devices (e.g., expandable stents) may be designed to treat a variety of medical conditions in the body. For example, some expandable stents may be designed to radially expand and support a body lumen and/or provide a fluid pathway for digested material, blood, or other fluid to flow therethrough following a medical procedure. Some medical devices may include radially or self-expanding stents which may be implanted transluminally via a variety of medical device delivery systems. These stents may be implanted in a variety of body lumens such as coronary or peripheral arteries, the esophageal tract, gastrointestinal tract (including the intestine, stomach and the colon), tracheobronchial tract, urinary tract, biliary tract, vascular system, etc.

In some instances it may be desirable to design stents to include sufficient flexibility while maintaining sufficient radial force to open the body lumen at the treatment site. However, in some stents, the compressible and flexible properties that assist in stent delivery may also result in a stent that has a tendency to migrate from its originally deployed position. For example, stents that are designed to be positioned in the esophageal or gastrointestinal tract may have a tendency to migrate due to peristalsis (i.e., the involuntary constriction and relaxation of the muscles of the esophagus, intestine, and colon which push the contents of the canal therethrough). Additionally, the generally moist and inherently lubricious environment of the esophagus, intestine, colon, etc. further contributes to a stent's tendency to migrate when deployed therein.

Therefore, in some instances it may be desirable to design a stent with anti-migration features to reduce the stent's tendency to migrate. Examples of medical devices including anti-migration features are disclosed herein.

SUMMARY

This disclosure provides design, material, manufacturing method, and use alternatives for medical devices. An example medical device may be a stent including an elongated tubular member having a longitudinal axis. The elongated tubular member is formed of at least one knitted filament forming a plurality of twisted knit stitches with rungs extending circumferentially between radially adjacent twisted knit stitches. Each twisted knit stitch is interconnected with a longitudinally adjacent twisted knit stitch forming a series of linked stitches. The elongated tubular member is configured to move between a radially collapsed configuration and a radially expanded configuration. In the collapsed configuration, the series of linked stitches form longitudinal columns, and in the expanded configuration, the series of linked stitches extend helically around the elongated tubular member.

Alternatively or in addition to any of the embodiments above, a length of the rungs in the collapsed configuration is less than a length of the rungs in the expanded configuration.

Alternatively or in addition to any of the embodiments above, each of the plurality of twisted knit stitches includes a loop portion and a crossed base portion.

Alternatively or in addition to any of the embodiments above, each loop portion, when in the expanded configuration, has a diameter between 1 mm and 5 mm.

Alternatively or in addition to any of the embodiments above, when in the expanded configuration, the rungs each have a length between 0.1 mm and 10 mm.

Alternatively or in addition to any of the embodiments above, the loop portion of at least some of the twisted knit stitches is wrapped around the crossed base portion of a longitudinally adjacent twisted knit stitch.

Alternatively or in addition to any of the embodiments above, when in the expanded configuration the rungs define an outer surface of the elongated tubular member and the crossed base portion of each twisted knit stitch extends radially outward from the outer surface.

Alternatively or in addition to any of the embodiments above, the crossed base portions form a raised ridge extending helically around the elongated tubular member in the expanded configuration.

Alternatively or in addition to any of the embodiments above, the raised ridge has a longitudinal cross-sectional wave shape, with a first slope facing a proximal end of the elongated tubular member, a crest, and a pocket facing a distal end of the elongated tubular member, wherein when inserted within a body lumen, the raised ridge resists distal movement while allowing removal in a proximal direction.

Alternatively or in addition to any of the embodiments above, the crest protrudes from the outer surface of the elongated tubular member between 0.5 mm and 5.0 mm.

Alternatively or in addition to any of the embodiments above, the stent includes a suture threaded through the loop portions of twisted knit stitches at a proximal end of the elongated tubular member.

Alternatively or in addition to any of the embodiments above, the elongated tubular member has a distal end region and a proximal end region, wherein at least one of the distal and proximal end regions is flared.

Alternatively or in addition to any of the embodiments above, the at least one knitted filament is only a single knitted filament.

Alternatively or in addition to any of the embodiments above, the elongated tubular member has a first longitudinal length in the collapsed configuration and a second longitudinal length in the expanded configuration, wherein the second longitudinal length is less than the first longitudinal length.

Another exemplary embodiment is a stent including an elongated tubular member. The elongated tubular member is formed of a plurality of interconnected loops separated circumferentially by rungs. The plurality of interconnected loops extend helically from a distal end to a proximal end of the elongated tubular member. Each loop has a loop portion and a crossed base portion. The loop portion of at least some of the loops is wrapped around the crossed base portion of a longitudinally adjacent loop. The elongated tubular member is configured to move between a radially collapsed configuration and a radially expanded configuration. In the collapsed configuration, the plurality of interconnected loops form longitudinal columns, and in the expanded configuration, the plurality of interconnected loops extend helically around the elongated tubular member.

Alternatively or in addition to any of the embodiments above, a length of the rungs in the collapsed configuration is less than a length of the rungs in the expanded configuration.

Alternatively or in addition to any of the embodiments above, the elongated tubular member is formed from only a single filament.

Alternatively or in addition to any of the embodiments above, when in the expanded configuration the rungs define an outer surface of the elongated tubular member and the crossed base portion of each loop extends radially outward from the outer surface.

Alternatively or in addition to any of the embodiments above, when the tubular member is bent into a curve, loop portions defining an outside curve elongate as a longitudinal spacing between longitudinally adjacent rungs increases, and loop portions defining an inside curve overlap one another more as the longitudinal spacing between longitudinally adjacent rungs decreases, allowing the tubular member to conform to a bend without kinking.

Another exemplary embodiment is method of forming a stent. The method includes attaching a plurality of threaded mandrels to a central mandrel, the threaded mandrels aligned parallel to the central mandrel and spaced apart around a circumference of the central mandrel. A shape memory filament is wrapped around a first threaded mandrel forming a first circumferential loop. The filament is extended circumferentially to a second threaded mandrel adjacent the first threaded mandrel. The filament is wrapped around the second threaded mandrel forming a second circumferential loop. The filament is extended circumferentially to and wrapped around successive adjacent threaded mandrels, forming additional loops. When the filament is extended back to the first threaded mandrel, the filament is moved longitudinally and again wrapped around the first threaded mandrel to form an additional loop. The filament is continued to be extended circumferentially to and wrapped around each threaded mandrel, moving longitudinally along the threaded mandrels, thereby forming a series of longitudinally spaced apart loops on each threaded mandrel. The shape memory filament is then heat set and the threaded mandrels are removed. Starting with the first circumferential loop, each circumferential loop is drawn through a longitudinally adjacent loop along the central mandrel to form a stent. Thereafter, the stent is removed from the central mandrel.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments in connection with the accompanying drawings, in which.

Figure 1:
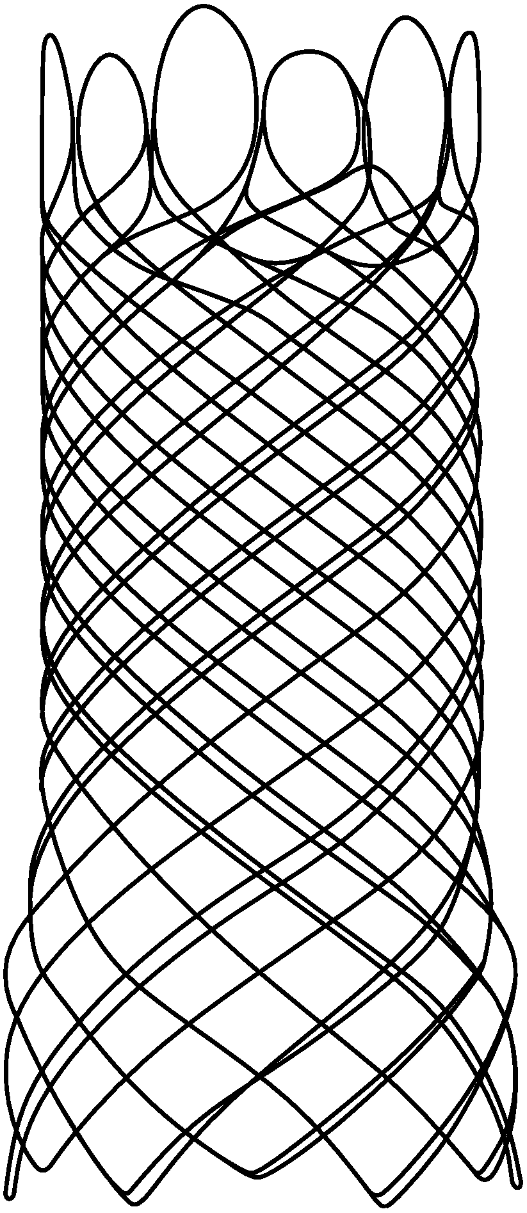
FIG. 1 PRIOR ART
FIG. 1 is a side view of a prior art braided stent.

While the disclosure is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the scope of the invention.

DETAILED DESCRIPTION

For the following defined terms, these definitions shall be applied, unless a different definition is given in the claims or elsewhere in this specification.

All numeric values are herein assumed to be modified by the term “about”, whether or not explicitly indicated. The term “about” generally refers to a range of numbers that one of skill in the art would consider equivalent to the recited value (i.e., having the same function or result). In many instances, the term “about” may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms “a”, “an”, and “the” include plural referents unless the content clearly dictates otherwise. As used in this specification and the appended claims, the term “or” is generally employed in its sense including “and/or” unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

In some instances, it may be desirable to provide an endoluminal implant, or stent, that can deliver luminal patency in a patient with an esophageal stricture or other medical condition. Such stents may be used in patients experiencing dysphagia, sometimes due to esophageal cancer. An esophageal stent may allow a patient to maintain nutrition via oral intake during cancer treatment or palliation periods.

Figure 2A:
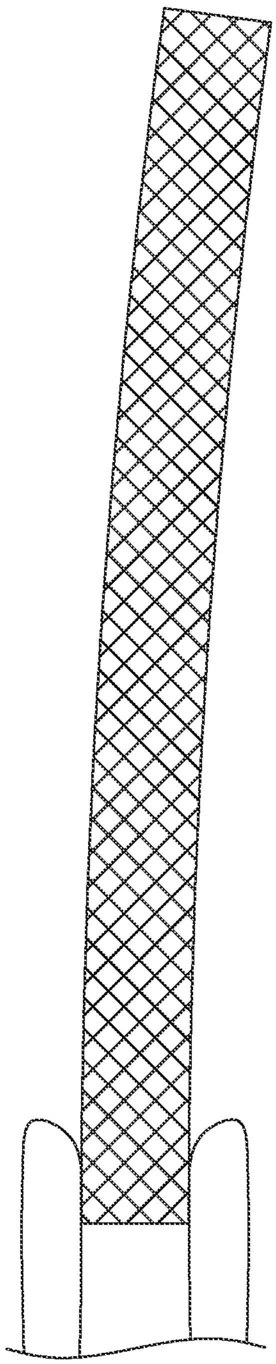
FIG. 2A PRIOR ART
FIGS. 2A, 2B, and 2C are side views of prior art braided stents showing conformability.
Figure 2B:
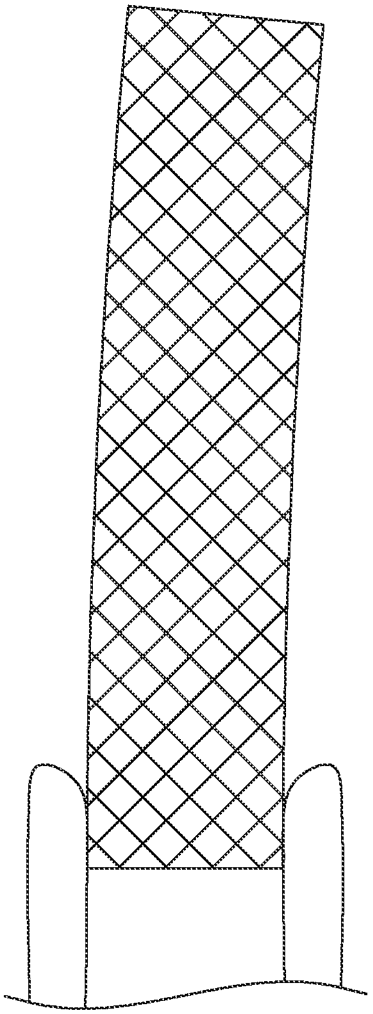
FIG. 2B PRIOR ART
Figure 2C:
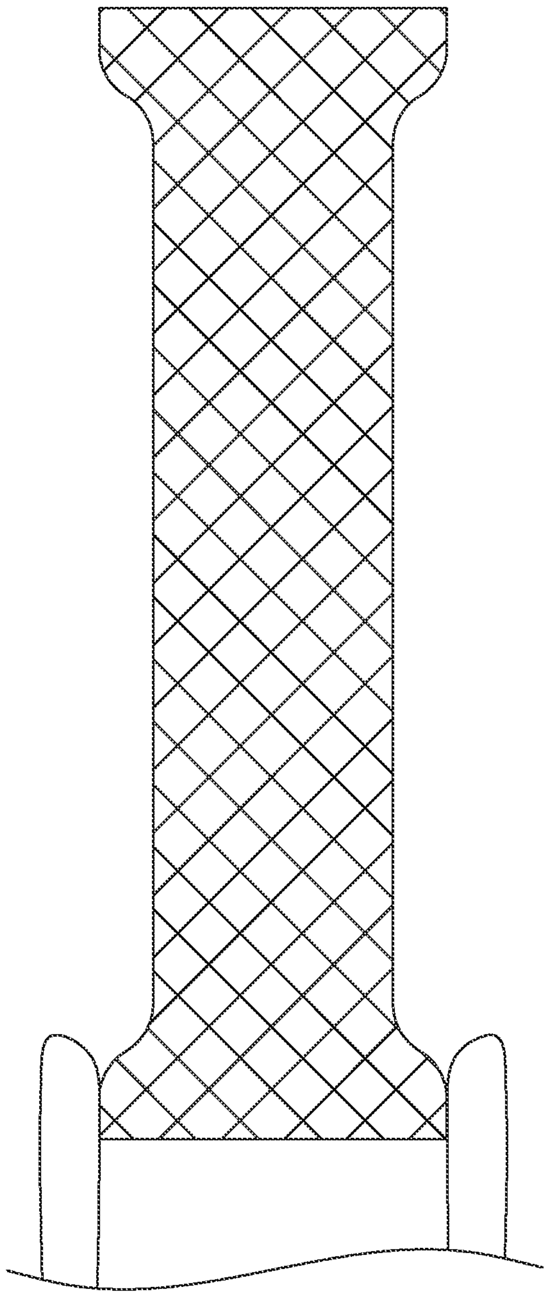
FIG. 2C PRIOR ART

A variety of self-expanding and balloon-expandable stents are available. Currently available braided and knitted stents offer good radial strength with minimal foreshortening which is desired for esophageal tracheo-bronchial and colonic applications. However, the currently available stents often lack the desired degree of conformability for some anatomical applications. For example, braided stents do not tend to conform to bends in the anatomy and instead tend to straighten the vessel or lumen in which they are placed. FIG. 1 illustrates a prior art braided stent. When the stent is held horizontally at one end, a conformable stent cannot support its own weight over the length of the stent. Braided stents generally have less conformability than knitted stents to anatomical bends. FIGS. 2A, 2B, and 2C illustrate three different prior art braided stents being held at the left end. As seen in the figures, the stents remain substantially rigid along their length and can support their own weight over the length of the stents.

Figure 3:
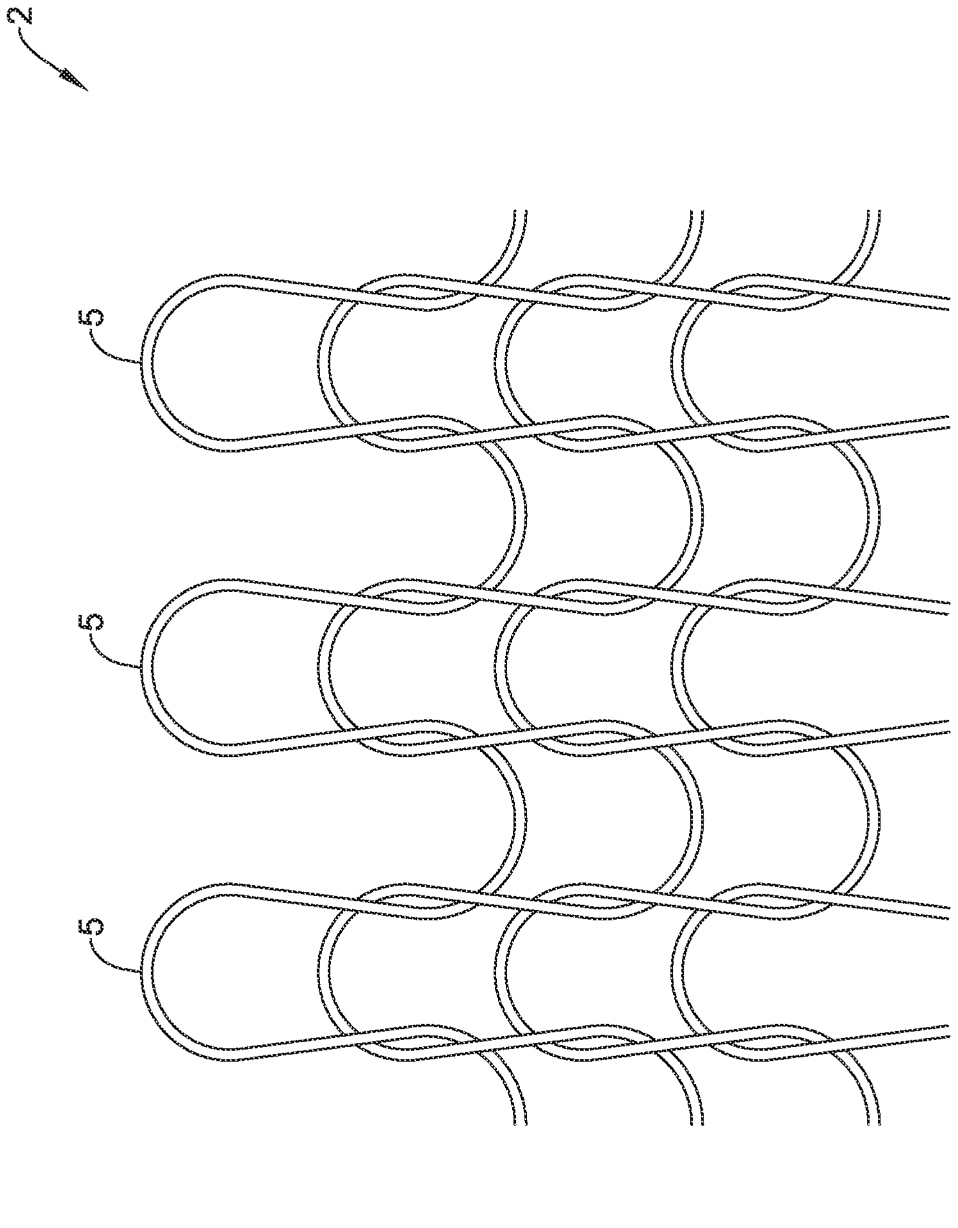
FIG. 3 PRIOR ART
FIG. 3 is an illustration of a portion of a prior art parallel knitted stent pattern.
Figure 4:
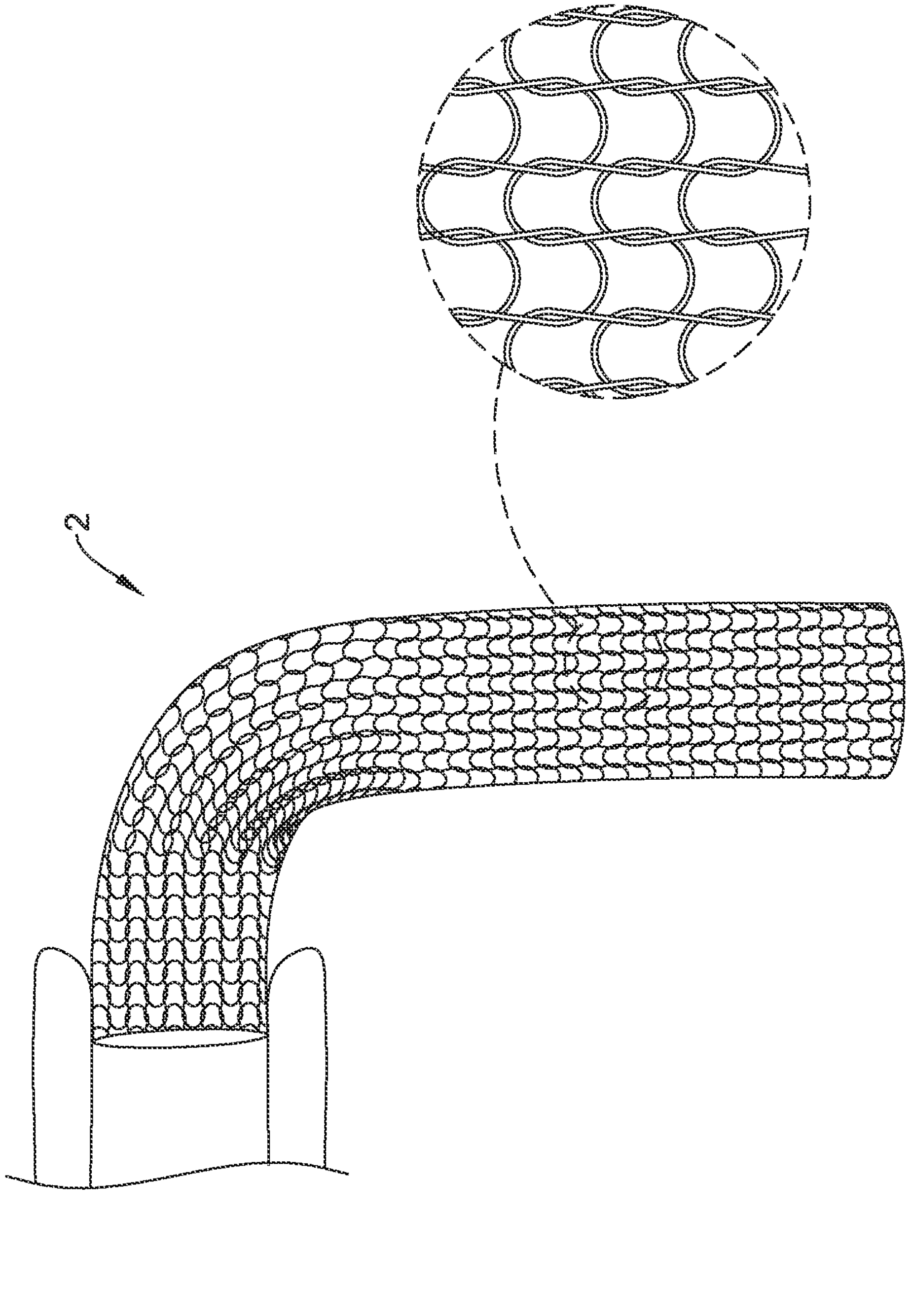
FIG. 4 PRIOR ART
FIG. 4 is a side view of a prior art parallel knitted stent showing conformability.

FIG. 3 illustrates a portion of a prior art self-expanding knitted stent 2. Conventional knitted self-expanding stents are generally designed using an automated weft knitting process that produces parallel columns 5 of knit stitches that run parallel to the longitudinal axis of the stent in both the expanded, relaxed configuration and the elongated, constrained configuration. The parallel knitted stent 2 provides good radial strength with minimal foreshortening which may be desirable in esophageal and trachea-bronchial applications as well as some post-bariatric surgery applications. However, this parallel knitted stent design may be difficult to constrain, especially into a coaxial delivery system and thus may be delivered using a system which may not offer a method of recapture, such as a crochet delivery system. Additionally, parallel knitted stent designs have a tendency to migrate in-situ. Esophageal stents are particularly susceptible to migration due to the peristaltic motion present in the esophagus. Migration of an esophageal stent may result in the stent migrating into the stomach which may cause major complications for the patient. Parallel knitted stents are generally more conformable to anatomical bends than braided stents because they are generally more flexible than braided stents. FIG. 4 shows an example parallel knitted stent 2 being held at the left end and exhibiting considerable conformability. However, conventional parallel knitted stents 2 tent to kink when placed in a torturous anatomical bend.

Figure 5A:
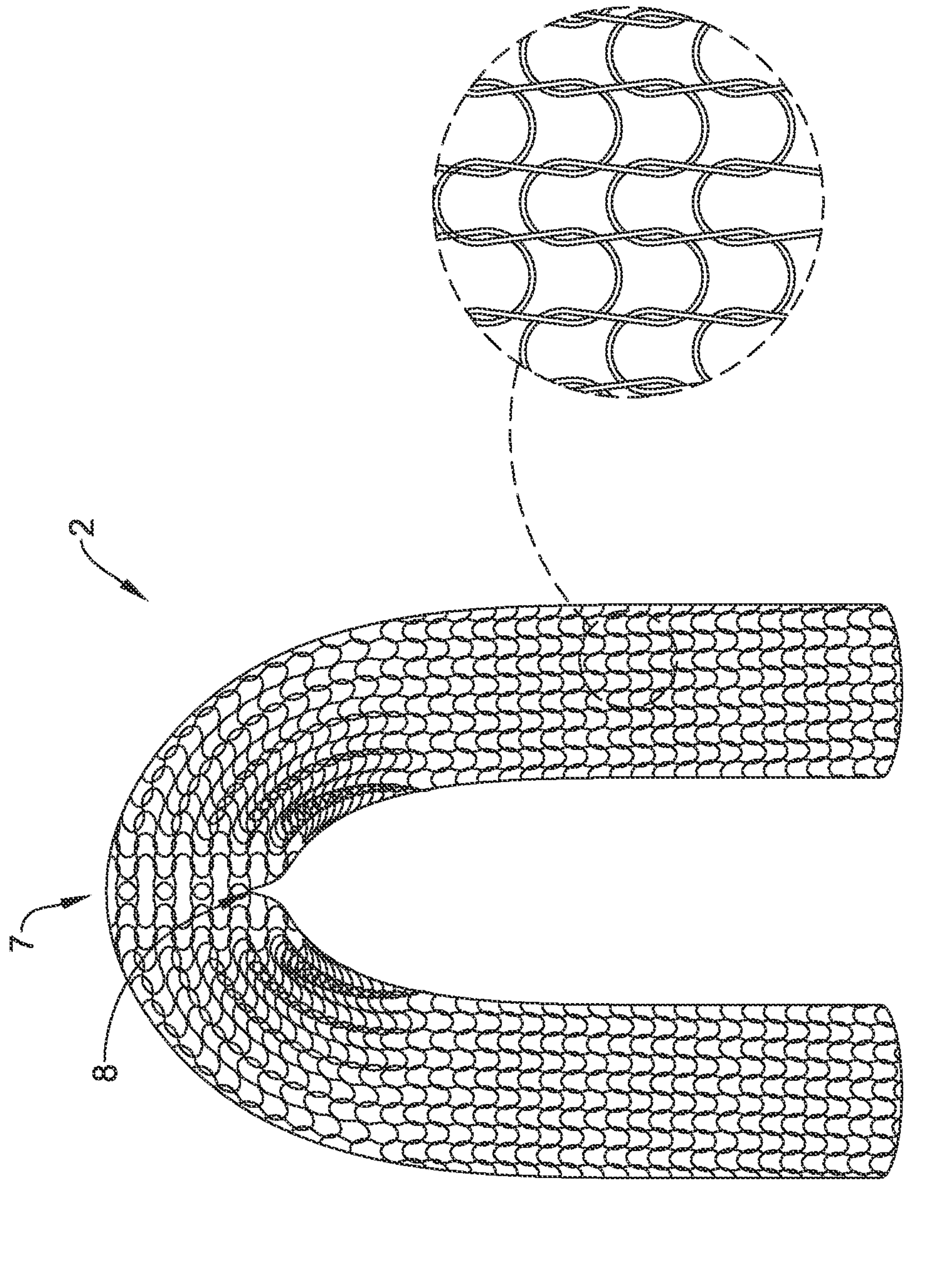
FIG. 5A PRIOR ART
FIGS. 5A and 5B are side views of a prior art parallel knitted stent bent approximately 180 degrees.
Figure 5B:
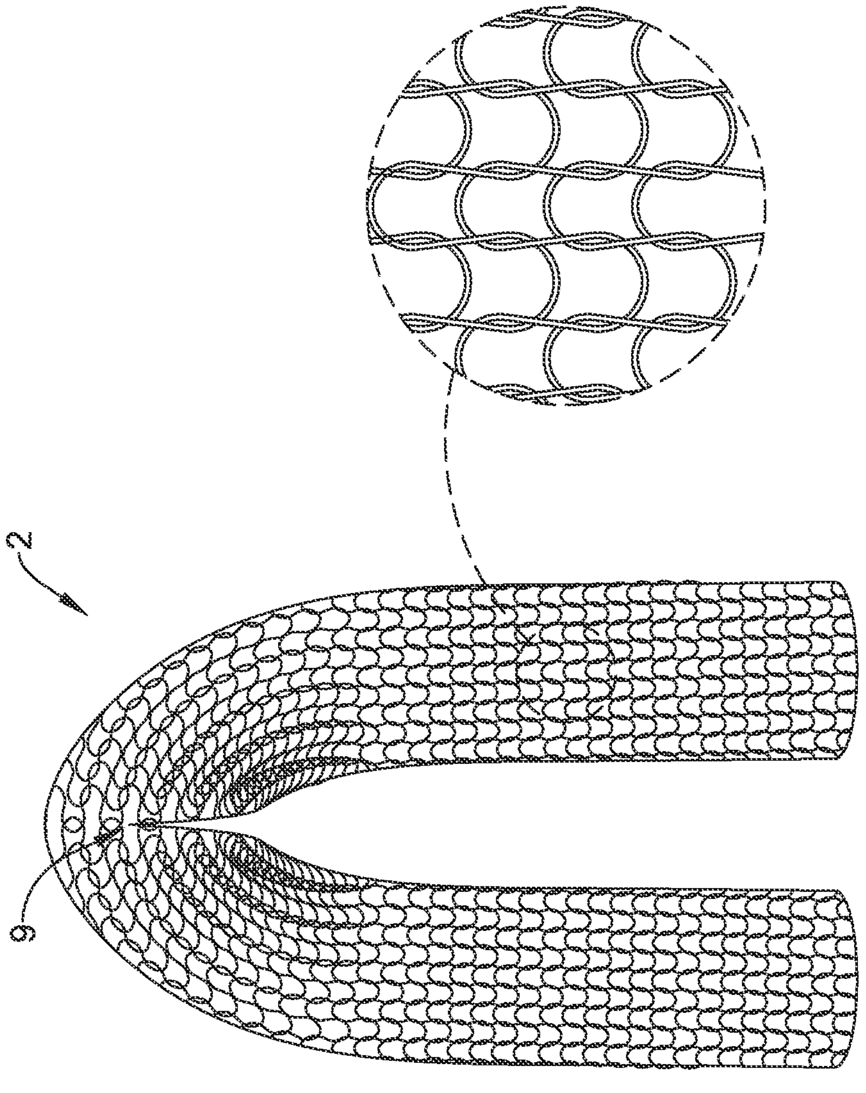
FIG. 5B PRIOR ART

FIGS. 5A and 5B illustrate a prior art parallel knitted stent 2 bent almost in half (approximately 180 degrees), to show the kinking that often occurs at severe bends in the anatomy. The parallel knitted pattern of the stent does not allow for stretching over the outside 7 of the bend or compression at the inside 8 of the bend, thus the stent forms a kink 9 at the bend. As the knitted pattern contains loops that run parallel to the stent (as seen in FIG. 3), there is build-up of material at the bend, which causes the stent 2 to kink. The kinking tendency shown in FIGS. 5A and 5B limits the bending capability of conventional parallel knitted stents.

An alternative knitted self-expanding stent is desired that is capable of delivery via a coaxial delivery system to a torturous anatomical bend, having similar conformability, radial forces, and foreshortening as previous parallel knitted stent configurations, but resists migration and kinking. While the embodiments disclosed herein are discussed with reference to esophageal and tracheo-bronchial stents, it is contemplated that the stents described herein may be used and sized for use in other locations such as, but not limited to: bodily tissue, bodily organs, vascular lumens, non-vascular lumens and combinations thereof, such as, but not limited to, in the coronary or peripheral vasculature, trachea, bronchi, colon, small intestine, biliary tract, urinary tract, prostate, brain, stomach and the like.

Figure 6:
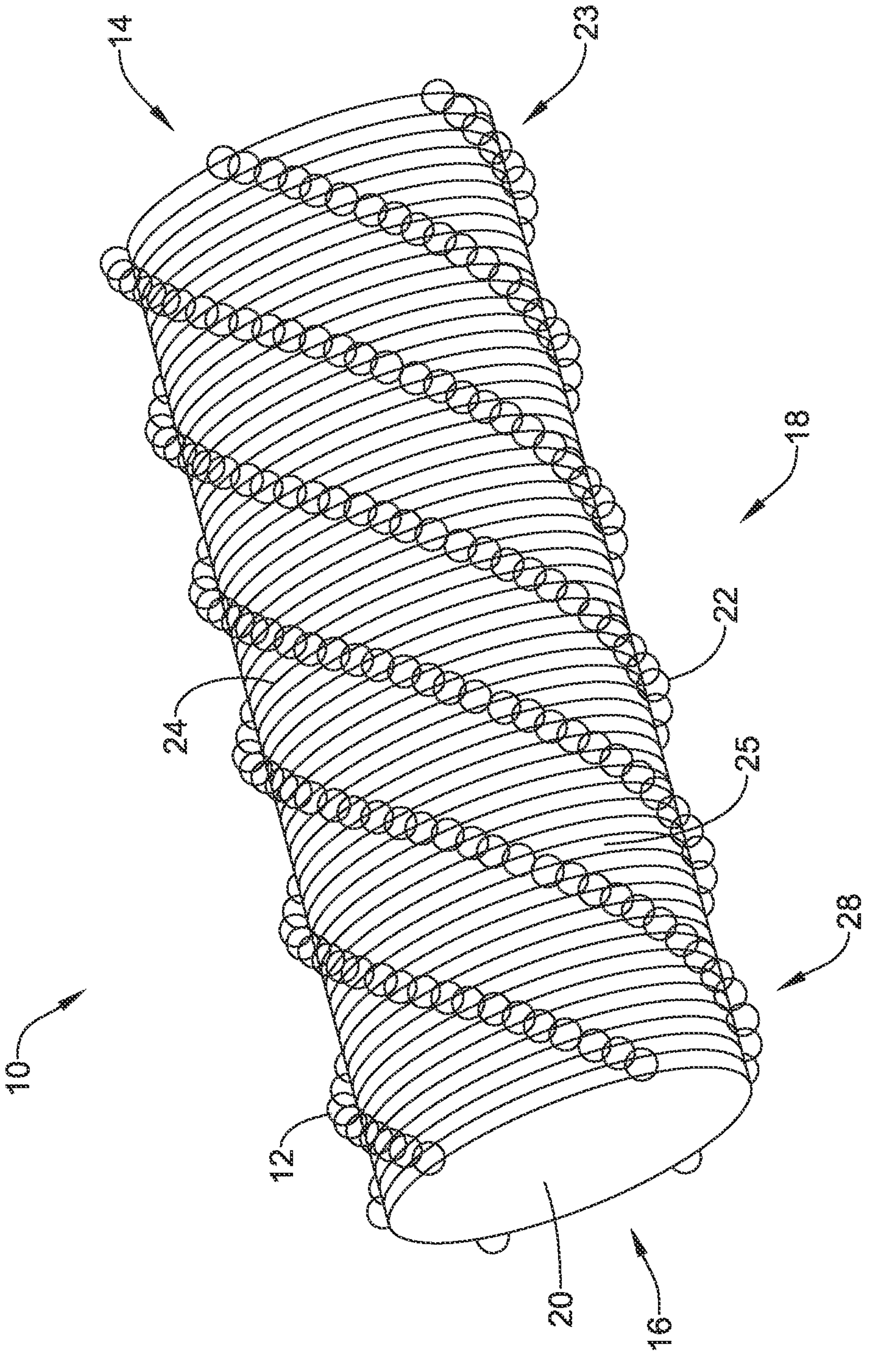
FIG. 6 is a perspective view of an illustrative stent.

FIG. 6 illustrates a perspective view of an example endoluminal implant, such as, but not limited to, a stent 10. In some instances, the stent 10 may be formed as an elongated tubular member 12. While the stent 10 is described as generally tubular, it is contemplated that the stent 10 may take any cross-sectional shape desired. The stent 10 may have a first, or proximal end 14, a second, or distal end 16, and an intermediate region 18 disposed between the proximal end 14 and the distal end 16. The stent 10 may include a lumen 20 extending from a first opening adjacent the proximal end 14 to a second opening adjacent to the distal end 16 to allow for the passage of food, fluids, etc.

The stent 10 may be fabricated from at least one filament 24 interwoven and defining open cells 25 and twisted knit stitches 22. In some examples, the stent 10 may be formed from only a single filament 24 interwoven with itself to form open cells 25 and twisted knit stitches 22. In some cases, the filament 24 may be a monofilament, while in other cases the filament 24 may be two or more filaments wound, braided, or woven together. In some instances, an inner and/or outer surface of the stent 10 may be entirely, substantially or partially, covered with a polymeric covering or coating. The covering or coating may extend across and/or occlude one or more, or a plurality of the open cells 25 and twisted knit stitches 22 defined by the filament 24. The covering or coating may help reduce food impaction and/or tumor or tissue ingrowth.

It is contemplated that the stent 10 can be made from a number of different materials such as, but not limited to, metals, metal alloys, shape memory alloys and/or polymers, as desired, enabling the stent 10 to be expanded into shape when accurately positioned within the body. In some instances, the material may be selected to enable the stent 10 to be removed with relative ease as well. For example, the stent 10 can be formed from alloys such as, but not limited to, Nitinol and Elgiloy®. Depending on the material selected for construction, the stent 10 may be self-expanding (i.e., configured to automatically radially expand when unconstrained). In some embodiments, fibers may be used to make the stent 10, which may be composite fibers, for example, having an outer shell made of Nitinol having a platinum core. It is further contemplated the stent 10 may be formed from polymers including, but not limited to, polyethylene terephthalate (PET). The stent 10 may be self-expanding. As used herein the term "self-expanding" refers to the tendency of the stent to return to a preprogrammed diameter when unrestrained from an external biasing force (for example, but not limited to a delivery catheter or sheath). The stent 10 may include a one-way valve (not shown), such as an elastomeric slit valve or duck bill valve, positioned within the lumen 20 thereof to prevent retrograde flow of gastrointestinal fluids.

In some instances, in the radially expanded configuration, the stent 10 may include a first end region 23 proximate the proximal end 14 and a second end region 28 proximate the distal end 16. In some embodiments, the first end region 23 and the second end region 28 may include retention features or anti-migration flared regions (not explicitly shown) having enlarged diameters relative to the intermediate region 18. Anti-migration flared regions, which may be positioned adjacent to the proximal end 14 and the distal end 16 of the stent 10, may be configured to engage an interior portion of the walls of the esophagus or other body lumen. It is contemplated that a transition from the cross-sectional area of the intermediate region 18 to the retention features or flared regions may be gradual, sloped, or occur in an abrupt step-wise manner, as desired.

In some embodiments, the first anti-migration flared region may have a first outer diameter and the second anti-migration flared region may have a second outer diameter. In some instances, the first and second outer diameters may be approximately the same, while in other instances, the first and second outer diameters may be different. In some embodiments, the stent 10 may include only one or none of the anti-migration flared regions. For example, the first end region 23 may include an anti-migration flare while the second end region 28 may have an outer diameter similar to the intermediate region 18. It is further contemplated that the second end region 28 may include an anti-migration flare while the first end region 23 may have an outer diameter similar to an outer diameter of the intermediate region 18. In some embodiments, the stent 10 may have a uniform outer diameter from the proximal end 14 to the distal end 16. In some embodiments, the outer diameter of the intermediate region 18 may be in the range of 15 to 25 millimeters. The outer diameter of the anti-migration flares may be in the range of 20 to 30 millimeters. It is contemplated that the outer diameter of the stent 10 may be varied to suit the desired application.

It is contemplated that the stent 10 can be made from a number of different materials such as, but not limited to, metals, metal alloys, shape memory alloys and/or polymers, as desired, enabling the stent 10 to be expanded into shape when accurately positioned within the body. In some instances, the material may be selected to enable the stent 10 to be removed with relative ease as well. For example, the stent 10 can be formed from alloys such as, but not limited to, Nitinol and Elgiloy®. Depending on the material selected for construction, the stent 10 may be self-expanding or require an external force to expand the stent 10. In some embodiments, composite filaments may be used to make the stent 10, which may include, for example, an outer shell or cladding made of Nitinol and a core formed of platinum or other radiopaque material. It is further contemplated the stent 10 may be formed from polymers including, but not limited to, polyethylene terephthalate (PET). In some instances, the filaments of the stent 10, or portions thereof, may be bioabsorbable or biodegradable, while in other instances the filaments of the stent 10, or portions thereof, may be biostable.

Figure 7:
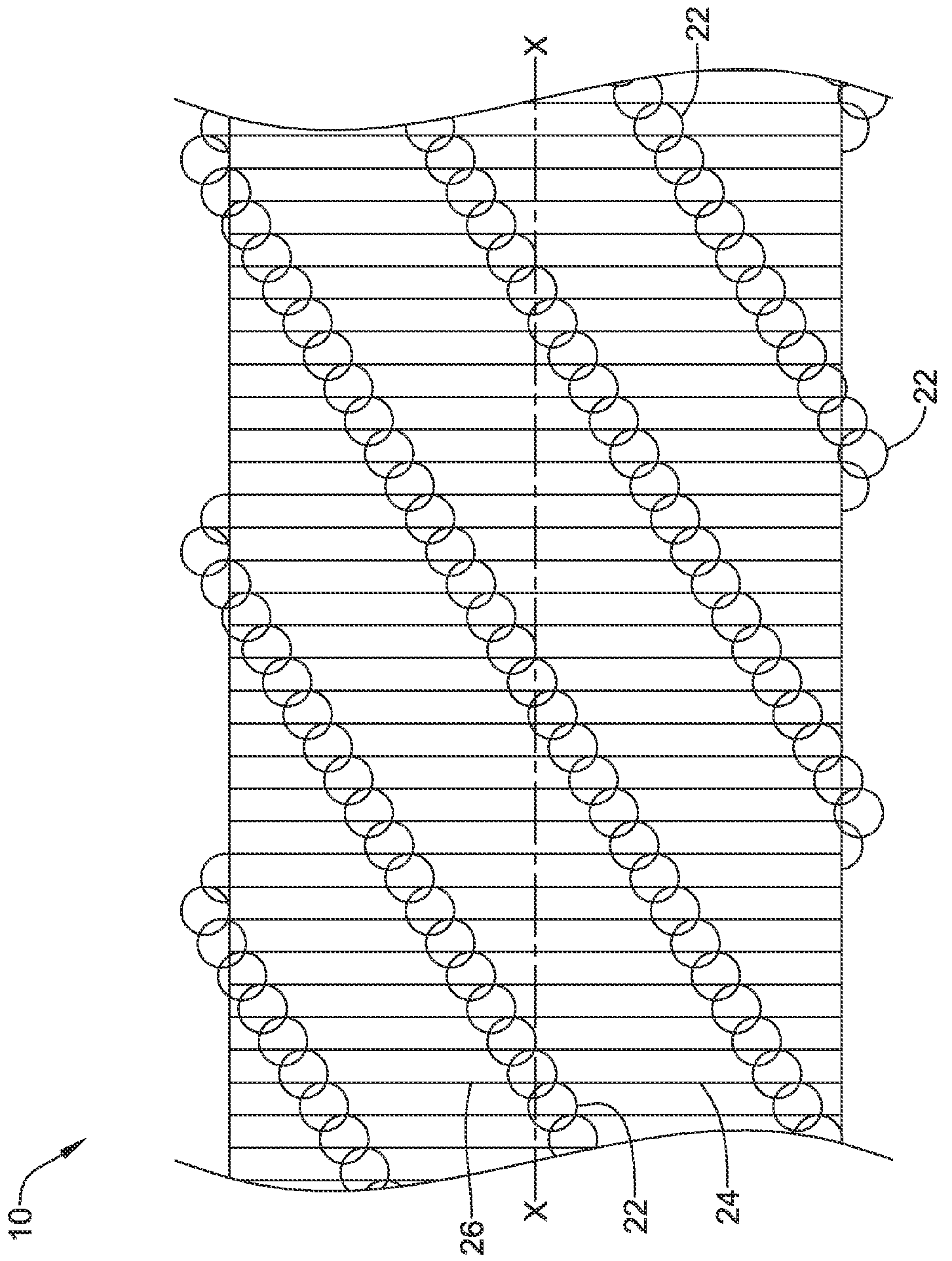
FIG. 7 is an enlarged top view of a portion of the illustrative stent of FIG. 6.

FIG. 7 illustrates the helical structure of the stent 10 when in the expanded, relaxed configuration. The stent 10 as illustrated may be fabricated from a single filament 24 forming twisted knit stitches 22 separated by elongate rungs 26 extending circumferentially between radially adjacent twisted knit stitches 22. Each twisted knit stitch 22 may be interconnected with a longitudinally adjacent twisted knit stitch 22 forming a series of linked stitches that extend helically around the stent in the expanded configuration, as shown in FIG. 7. The interconnected twisted knit stitches 22 may extend helically around the stent 10 along the entire length of the stent 10. In some embodiments, when the stent 10 is in a fully relaxed state, the rungs 26 may extend substantially perpendicular to the longitudinal axis x-x of the stent 10, as shown in FIG. 7. In some embodiments, the rungs 26 may be between 0.1 mm and 10.0 mm in length in the expanded configuration. In other examples, the rungs may have a length between 1 mm and 5 mm. In still other examples, the rungs 26 may have a length between 2 mm and 3 mm.

Figure 8:
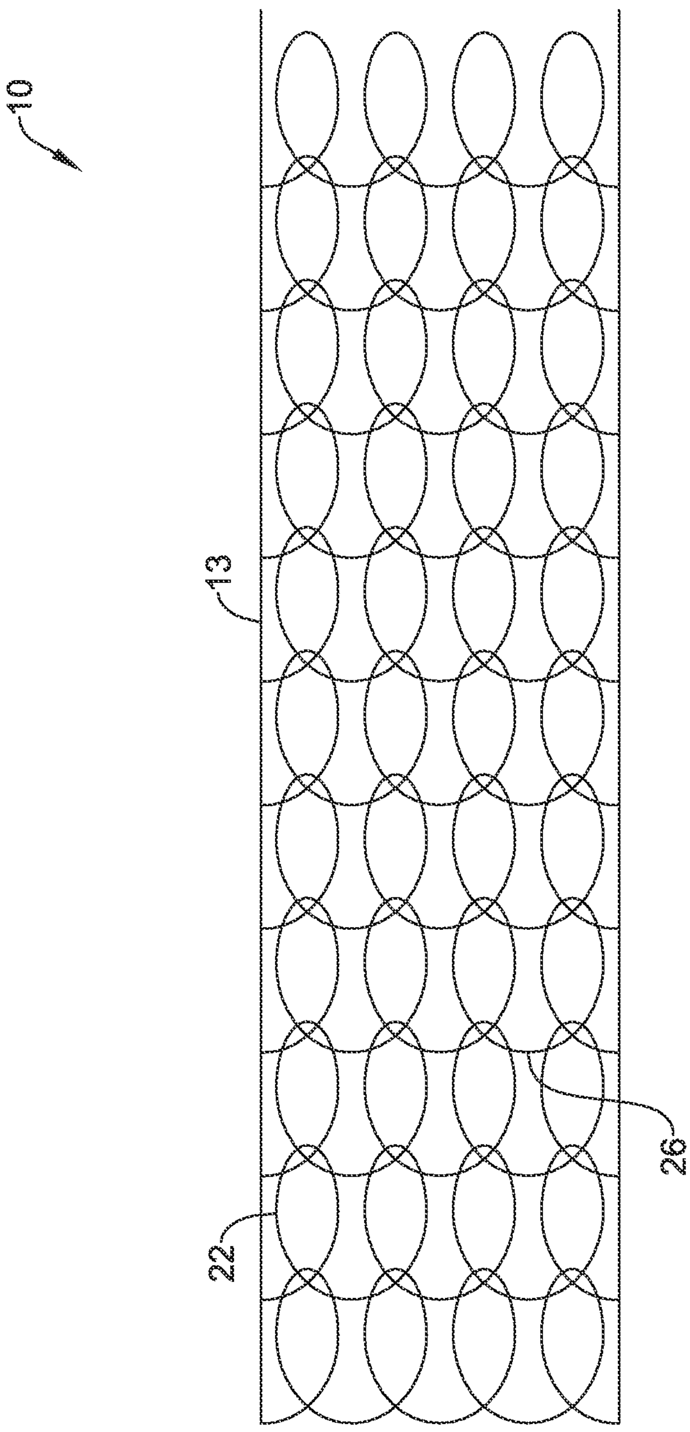
FIG. 8 is an illustration of the stent of FIG. 6 in a collapsed configuration.
Figure 9:
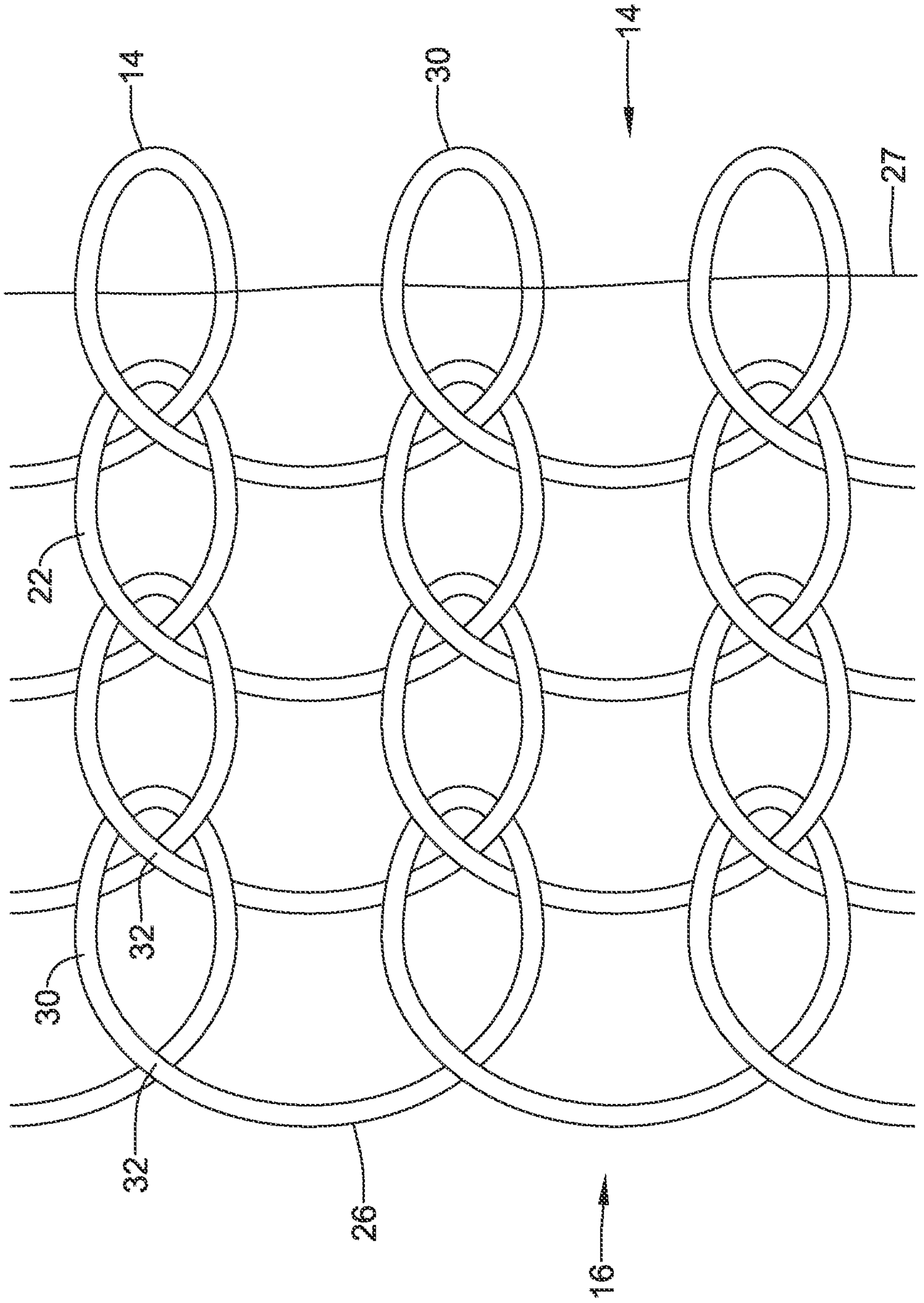
FIG. 9 is an enlarged view of a portion of the stent of FIG. 8.

FIG. 8 illustrates the stent 10 in a collapsed configuration disposed within a delivery sheath 13. When the stent 10 is collapsed and elongated as it is inserted into the delivery sheath 13, the helical interconnected twisted knit stitches 22 straighten into longitudinal columns, as shown in FIG. 8. The twisted knit stitches 22 elongate and the rungs 26 become shorter. The structure of the twisted knit stitches 22 in the collapsed, constrained configuration, is illustrated in FIG. 9. Each twisted knit stitch 22 may include a loop portion 30 and a crossed base region 32. The loop portions 30 may be wrapped around the crossed base regions 32 of longitudinally adjacent twisted knit stitches 22. The crossed base regions 32 are distal of the loop portions 30, such that at the distal end 16 of the stent, the crossed base regions 32 define an atraumatic structure, as shown in FIG. 9. While the loop portions 30 have an elongate or oval shape in the collapsed configuration shown in FIG. 9, the loop portions 30 may have a generally circular shape in the expanded configuration, as shown in FIG. 7. In some examples, the loops 130 may have a diameter of between 1 mm and 5 mm in the expanded configuration. In other examples, the loops 130 may have a diameter of between 2 mm and 3 mm.

The proximal end 14 of the stent 10 may be defined by a series of free loop portions 30. In some embodiments, a tether or suture 27 may be threaded through the free loop portions 30 at the proximal end to facilitate removal of the stent 10. The retrieval suture 27 may be used to collapse and retrieve the stent 10, if so desired. For example, the retrieval suture 27 may be pulled like a drawstring to radially collapse the proximal end 14 of the stent 10 to facilitate removal of the stent 10 from a body lumen. The size of the free loop portions 30 at the proximal end may be increased or decreased to increase or decrease, respectively, the amount of tissue ingrowth at the proximal end achieved upon implantation of the stent 10.

In the expanded configuration, the rungs 26 define an outer surface 40 of the stent 10 and the crossed base regions 32 of the twisted knit stitches 22 extend radially outward from the outer surface 40. The crossed base regions 32 form a raised ridge 34 extending helically around the stent 10. In some examples, the helical ridge 34 may have a longitudinal cross-sectional wave shape, with a proximal facing slope 35, a crest 36, and a pocket 37 facing a distal end 16 of the elongated tubular member. In some examples, the crest 36 may protrude from the outer surface 40 between 0.5 mm and 5.0 mm. In a particular example, the crest 36 may protrude 1.5 mm from the outer surface 40. The distance is essentially the diameter of the loop 30, and the minimum distance is dependent on the diameter of the filament 24. For example, 3 thou to 14 thou wires (0.0762 mm to 0.3556 mm) may be used as the filament 24. In one example, a 6 thou wire (0.1524 mm) was used as the filament 24.

The space between the helical ridges 34 may define channels 38 extending between crests 36 of adjacent ridges 34. The channels 38 may provide a drainage feature for the stent 10. The ridges 34 may engage the tissue wall, while leaving at least a portion of the channels 38 spaced from the tissue wall, providing for drainage of fluid along the entire length of the stent 10. A covering or graft disposed over the stent or within the lumen may aid in defining the channels 38.

Figure 11:
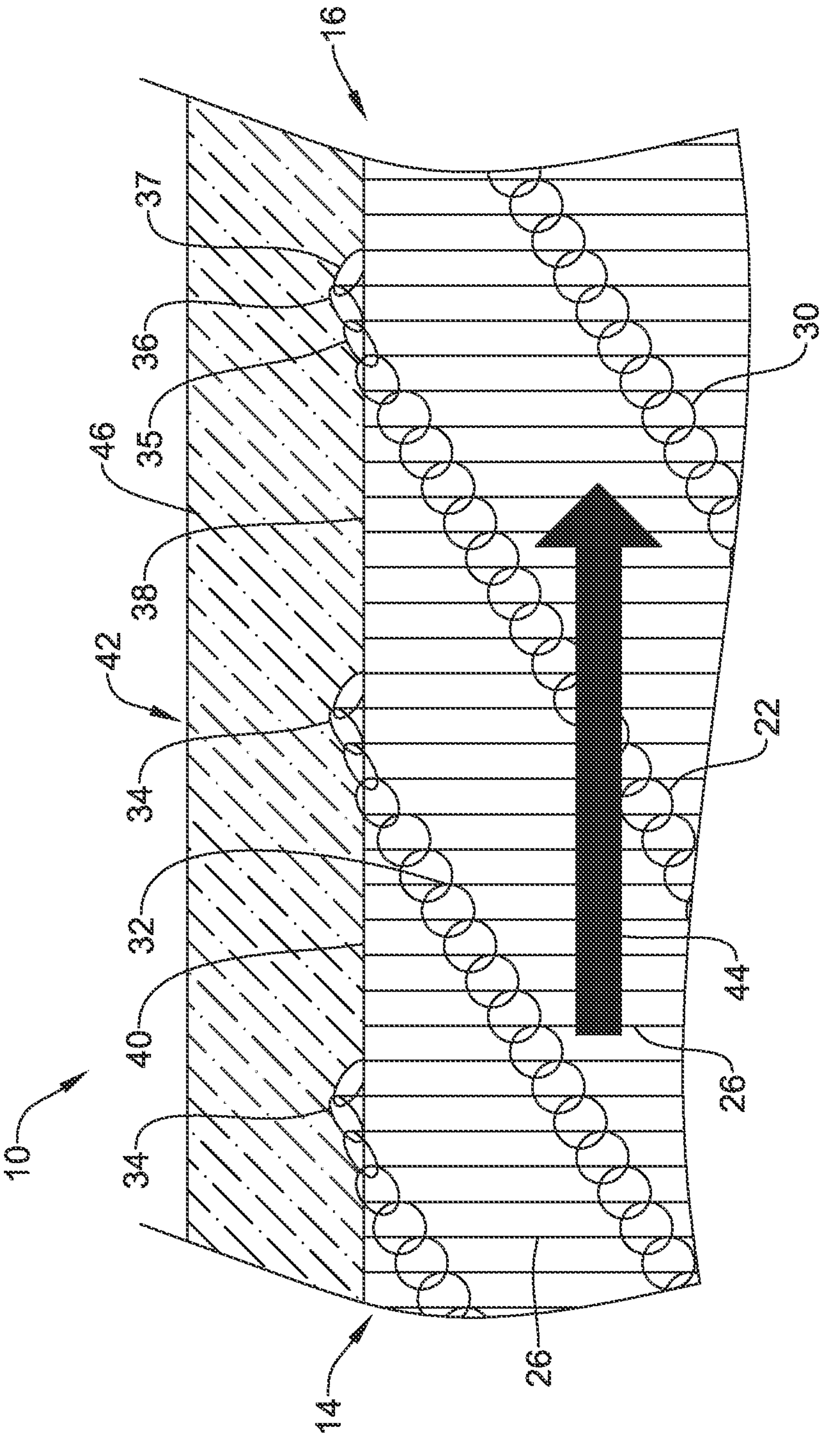
FIG. 11 is an illustration of a portion of the stent of FIG. 6 disposed within a body lumen.

FIG. 11 illustrates the stent 10 disposed with a body lumen 42. The wave shape of the ridge 34 provides strong anti-migration properties in one direction and less in the opposite direction. The stent 10 may be loaded into a delivery sheath and placed in a body lumen in the preferred orientation to optimize resistance to the migration force on the stent, as shown in FIG. 11. This unique anti-migration feature may also provide a benefit during removal of the stent, as during removal the stent may be pulled in the direction with less anti-migration properties. This feature may make removal of the stent very easy for the physician without compromising any of the overall strong anti-migration properties of the stent.

Figure 10:
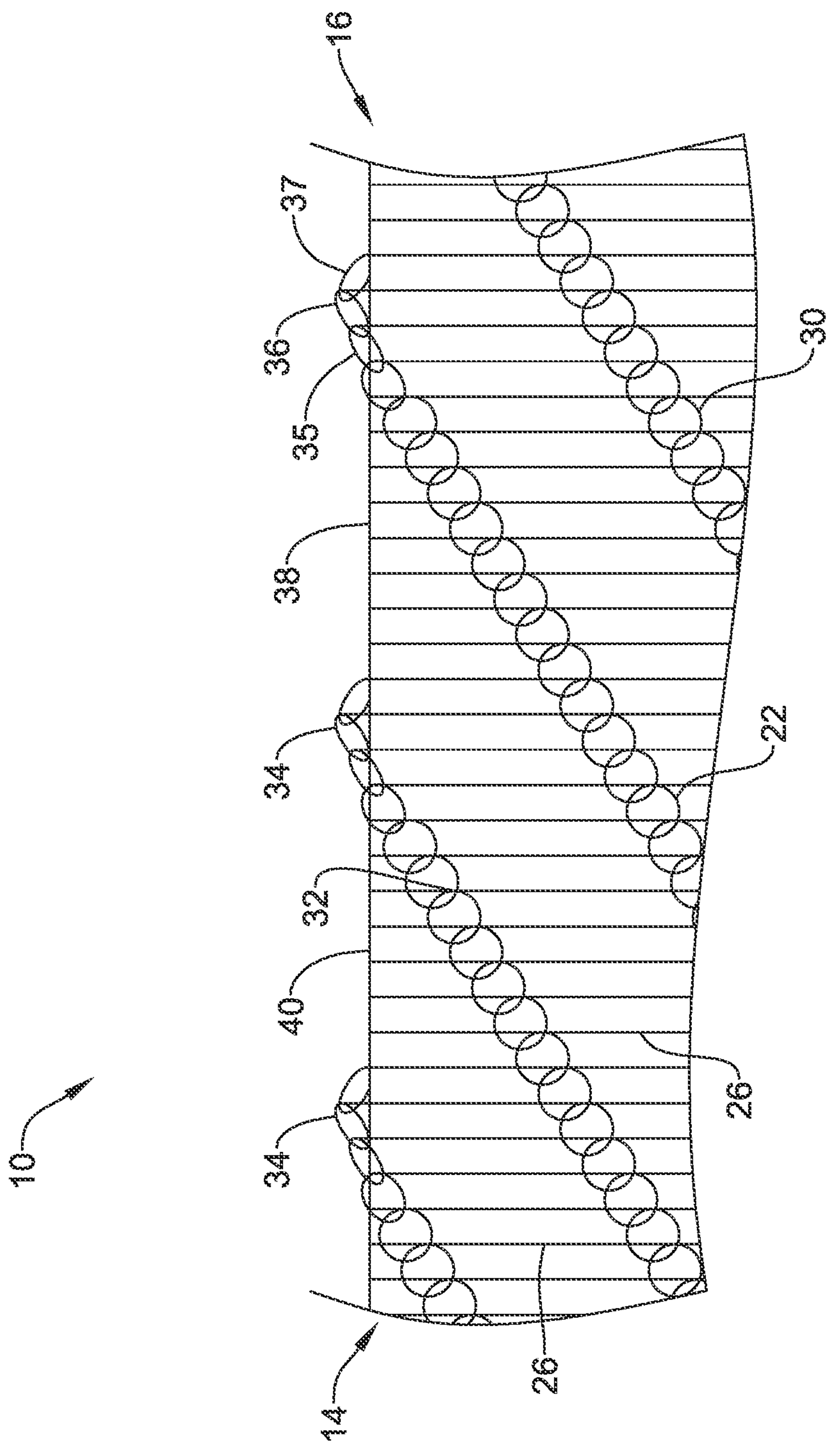
FIG. 10 is an enlarged side view of a longitudinal edge of the illustrative stent of FIG. 6.

When migration forces 44, such as peristalsis when the stent is disposed within the esophagus or intestine, are exerted in a distal direction on the stent 10, the wave crest 36 provides resistance by pushing into the vessel wall 46, and the pocket 37 engages a portion of the vessel wall 46, as seen in FIG. 11, thereby preventing migration of the stent 10. The crest 36 is devoid of any sharp edge, barb, or quill. Rather, the crest 36 defines a smooth yet defined edge, as shown in FIG. 10. The anti-migration provided by the crest 36, is exhibited for each raised ridge 34 along the entire length of the stent 10. The wave shape of the ridge 34, in particular the gradual proximal facing slope 35, allows for removal of the stent 10 in the proximal direction without damage to the vessel wall 46.

The twisted knit stitches 22, and in particular, the loop portions 30 may be configured to match the level of tissue ingrowth desired and/or required. For example, increased tissue ingrowth may be achieved by increasing the number of loop portions 30 around the circumference of the stent 10. The pitch and/or angle of the helices may also be increased, and the size of the loop portions 30 may be altered. The configuration of the loop portions 30 may have a more pronounced effect on the tissue ingrowth in stents having a bare metal composition, devoid of any covering or graft.

The peristaltic motion in the esophagus and intestines occurs along the longitudinal surface of the vessel wall. Existing parallel knitted stents have raised loops in a straight formation along the entire length of the stent. The forces transferred to such stents by peristalsis is thus constantly exerted on the entire length of the stent. However, due to the helical ridges 34 of the stent 10, there is no direct transfer of force along the entire length of the stent. Instead, the vessel wall 46 exhibits force on the raised ridge 34 of the stent 10, but the force is intermittent, because no force is transferred to the outer surface 40 defined by the rungs 26 of the stent 10.

Figure 12A:
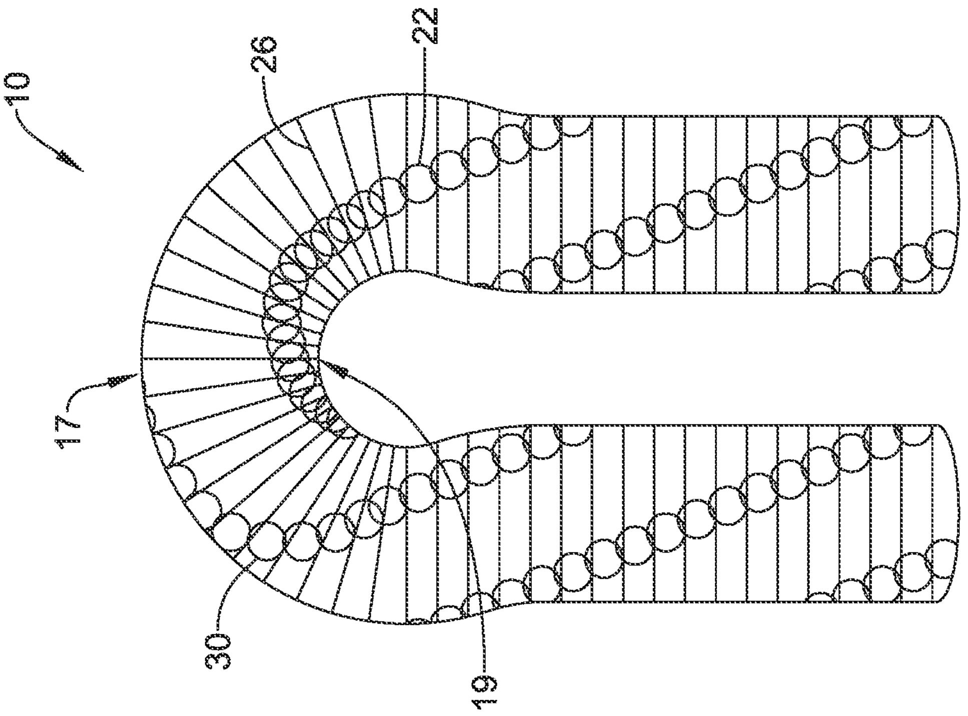
FIGS. 12A and 12B are side views of the stent of FIG. 6 bent approximately 180 degrees.

FIGS. 12A and 1B illustrate the conformability of the stent 10. The design of the helical series of interconnected twisted knit stitches 22 allows the stent 10 to conform to bends in a vessel without kinking. The increased conformability of the helical stent 10 is due to the ability of the circular loop knit design to elongate and compress at lower forces than the conventional knitted stents with parallel knit stitches. The loop portions 30 defining the outside curve 17 of the bend elongate as a longitudinal spacing between longitudinally adjacent rungs 26 increases, and the loop portions 30 defining the inside curve 19 of the bend overlap one another more as the longitudinal spacing between longitudinally adjacent rungs 26 decreases. The outside curve 17 expands under small tension forces and the inside curve 19 compresses under small compression forces on the smaller radial surface. This combination of loop portions 30 elongating and compressing allows the stent 10 to bend without kinking.

Figure 12B:
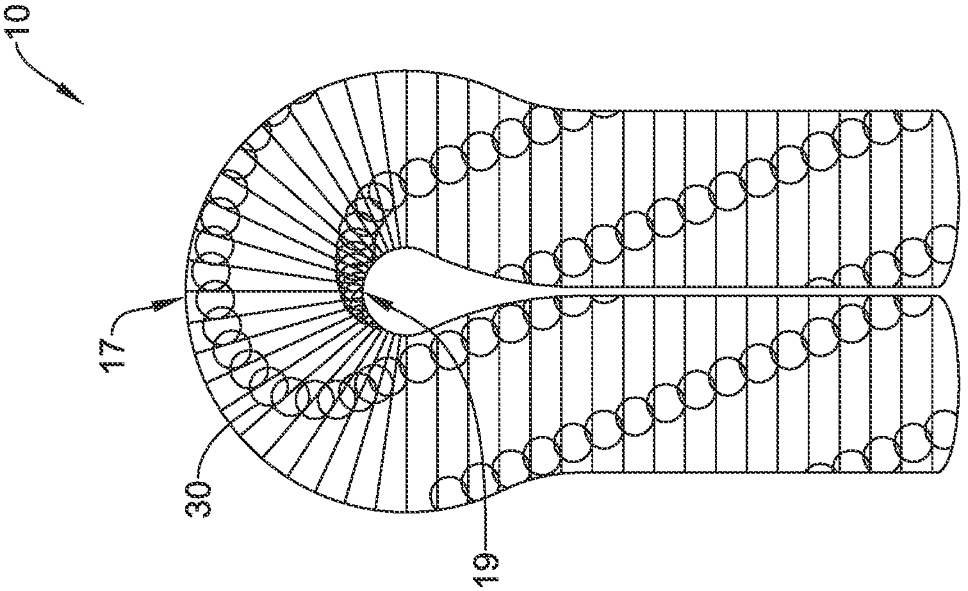

In particular, FIG. 12B illustrates the stent 10 bent more than 180 degrees without any kink at the inside curve 19 of the bend. Compare the bending/kinking properties of the conventional stent 2 with parallel knit stitches shown in FIGS. 5A and 5B with the stent 10 having twisted knit stitches including loop portions extending helically around the stent, as shown in FIGS. 12A and 12B. Kinking is evident in the conventional stent 2 shown in FIGS. 5A and 5B, while the helical stent 10 has the ability to conform around a torturous bend without kinking or closing off the stent, as shown in FIGS. 12A and 12B. As the conventional stent 2 contains loops that run parallel to the longitudinal axis of the stent, as shown in FIG. 3, there is a material build up at the bend, which causes the stent to kink. Due to the helical configuration of the stent 10, there is less material build up at the bend. The material build up is offset due to the loop portions 30 running at an angle to the bend.

Figure 13:
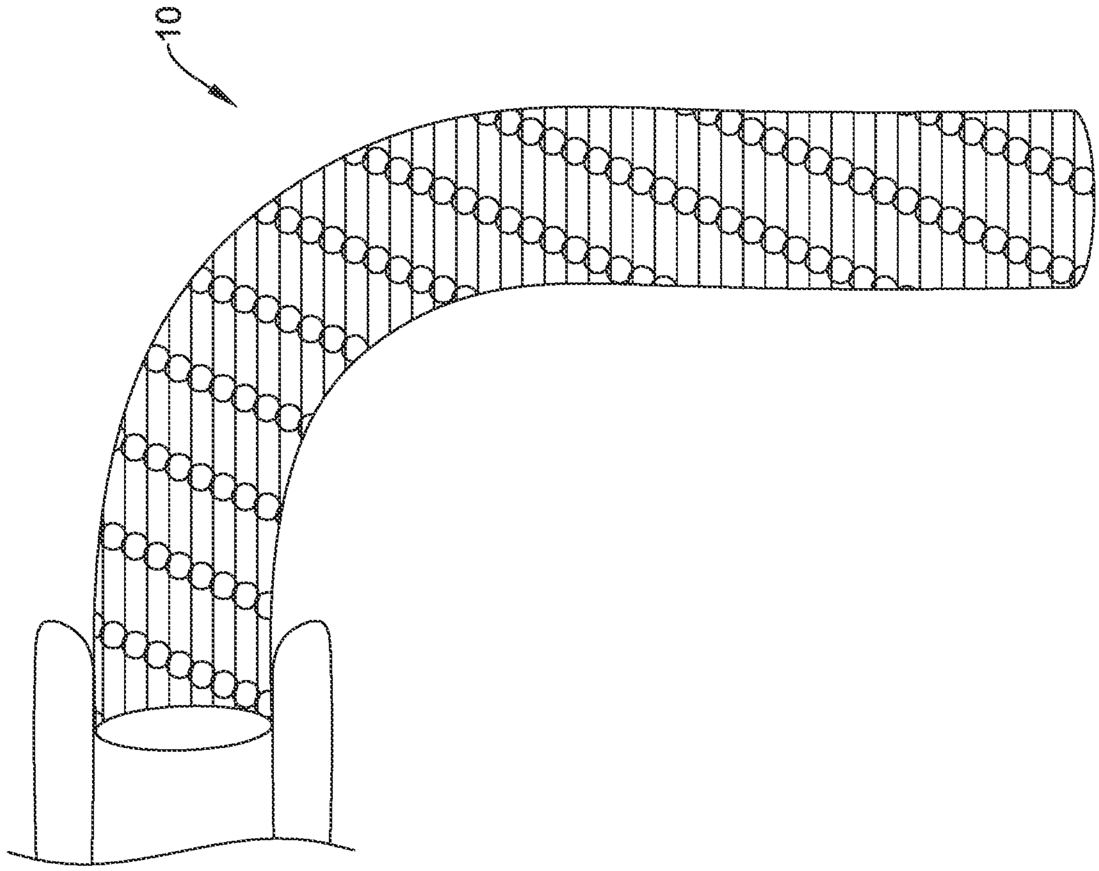
FIG. 13 is a side view of the stent of FIG. 6 showing conformability.

The stent 10 with its helical configuration of twisted knit stitches 22, shown in FIGS. 6-12B, exhibits conformability, shown in FIG. 13 being held at the left end, significantly increased over conventional braided stents, shown in FIGS. 2A-2C, and similar to the conventional parallel knitted stent 2 shown in FIG. 4. The stent 10 is thus conformable to torturous bends in the anatomy, however as discussed above, the stent 10 avoids the kinking seen in conventional parallel knitted stents 2.

Figure 14A:
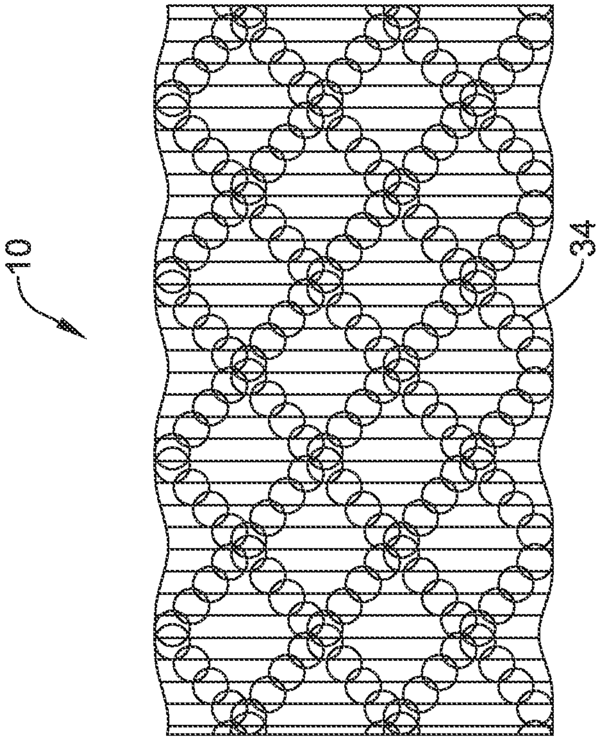
FIGS. 14A and 14B illustrate the spring characteristic of the stent of FIG. 6.
Figure 14B:
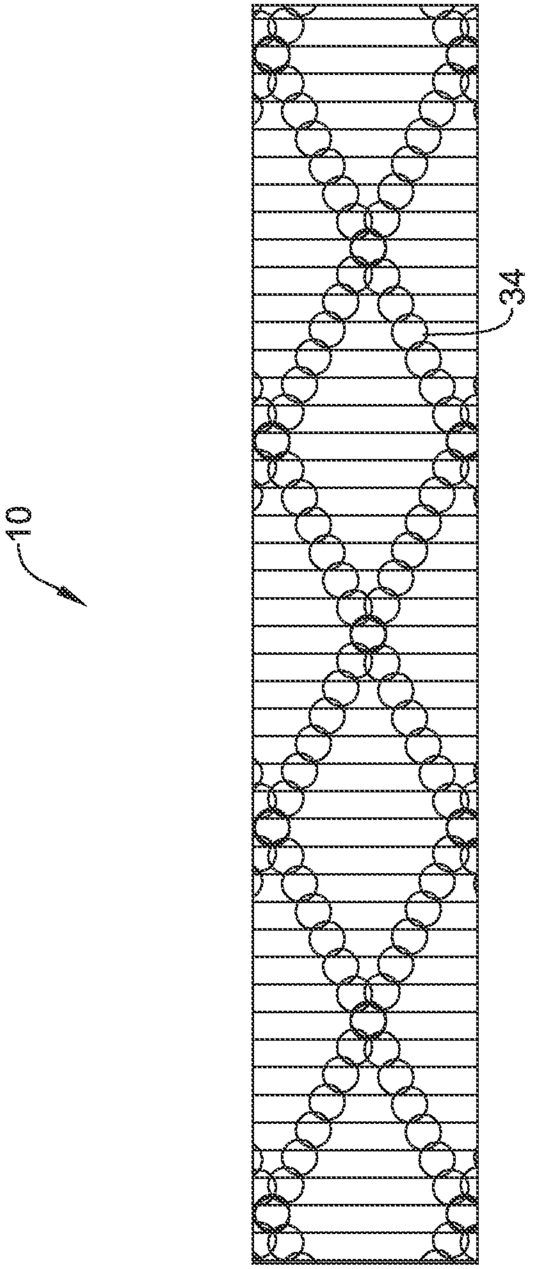

The stent 10 behaves like a spring in the deployed, fully expanded configuration. This is not a property of conventional parallel knitted or braided metal stents. As seen in FIG. 14A, in the fully expanded configuration, the stent 10 has a series of helical ridges 34 of twisted knit stitches. When the stent 10 is partially stretched, the helical ridges 34 straighten, as shown in FIG. 14B. When the stent 10 is stretched longitudinally into the collapsed configuration in order to constrain the stent 10 on a co-axial delivery system, the ridges 34 may be parallel, as shown in FIG. 8. In some examples, the stent 10 may have a first longitudinal length in the collapsed configuration and a second longitudinal length in the expanded configuration, wherein the second longitudinal length is less than the first longitudinal length.

During deployment, the stent 10 twists in a corkscrew manner as it returns to its original helical shape. This corkscrew twisting motion during deployment may help the stent 10 engage the vessel wall. This spring type expansion of the stent 10 means that the stent 10 will resist the peristaltic forces exerted on it, returning to its original shape and/or position after any elongation occurs during peristalsis. When the stent 10 experiences the peristaltic motion pushing along the stent 10, the part of the stent 10 expands radially ahead of the motion, similar to a spring. The increased diameter of the stent 10 provides further anti-migration to the stent 10. Once the peristaltic motion has passed down the length of the stent 10, the stent 10 will begin to return to its original position.

Figure 15A:
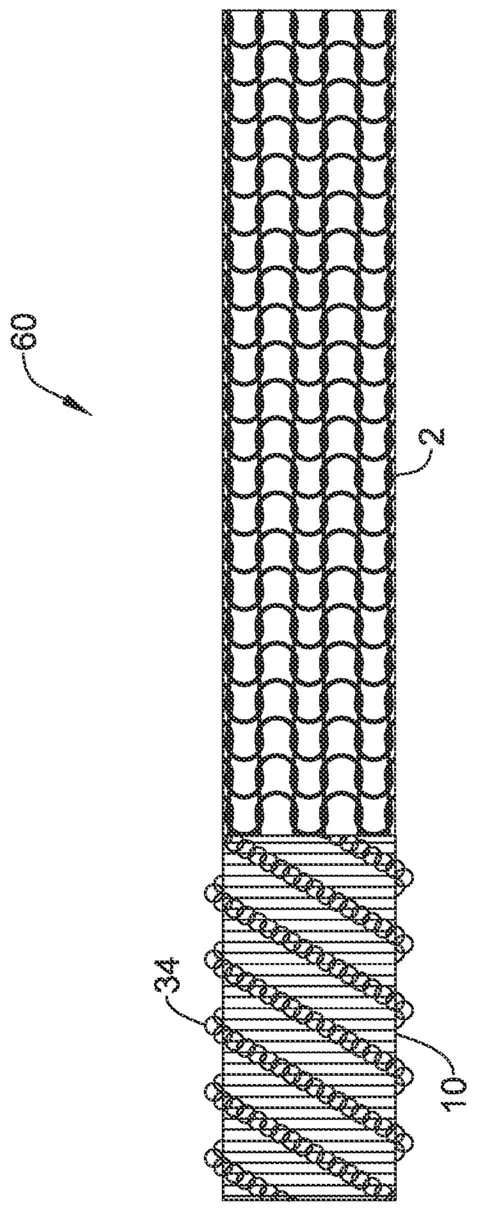
FIGS. 15A and 15B are illustrations of alternative illustrative stents.
Figure 15B:
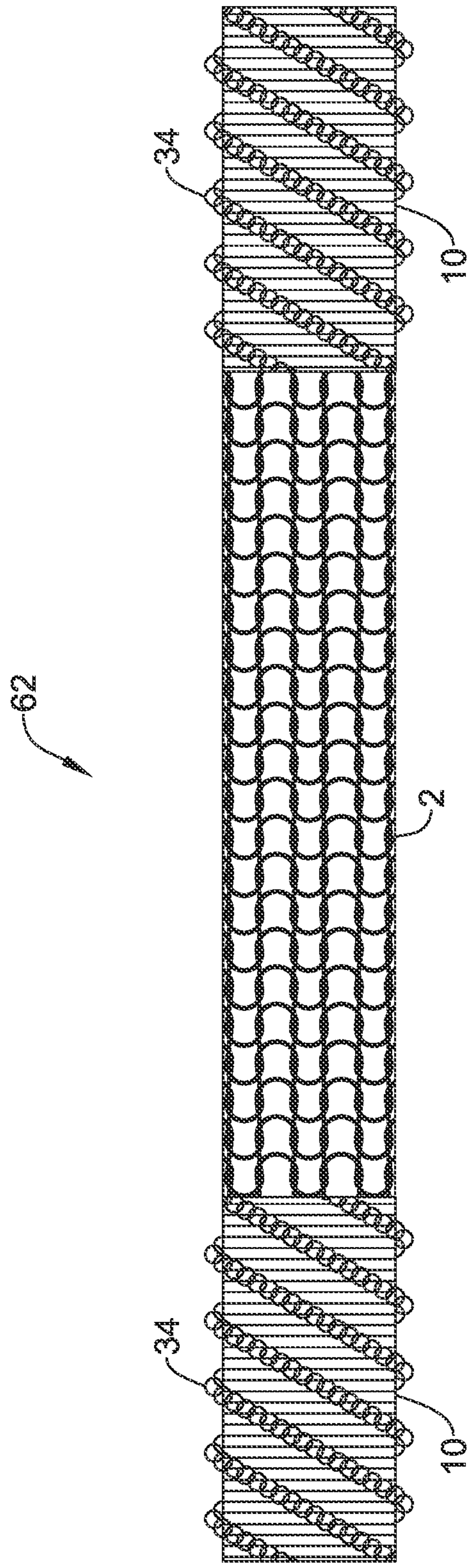

FIGS. 15A and 15B illustrate combination stents 60, 62, in which one or more stent 10 with helical ridges 34 is combined with one or more conventional parallel knitted stent 2. In particular, the stent 10 may be attached at one or both ends of the parallel knitted stent 2. Such a combination stent may offer circumferential anti-migration from the helical ridges 34 on one or both ends of the combination stents 60, 62. In some examples, the combination stents 60, 62 may have a 50/50 ratio of stent 10 to stent 2. In one example of the combination stent 62, the stents 10 making up the ends could be up to 25% of the overall length of the stent 62.

Figure 16A:
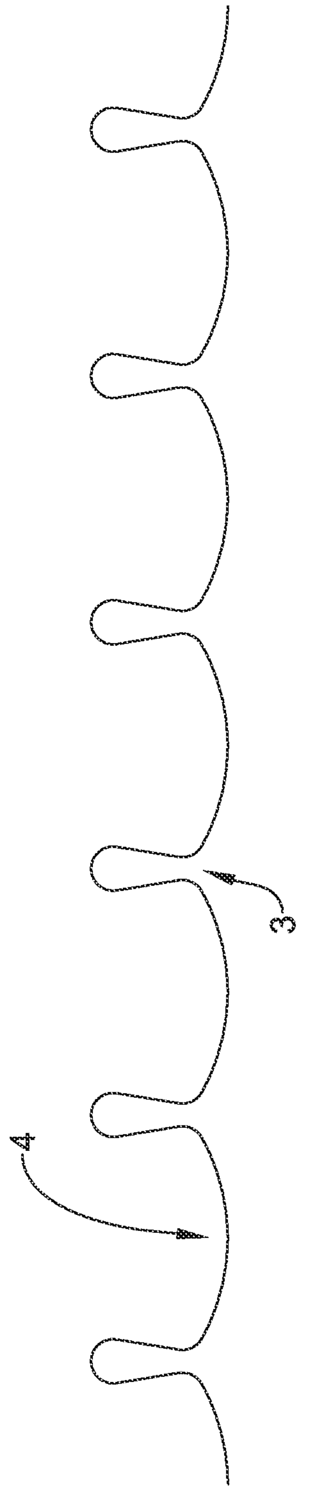
FIG. 16A PRIOR ART
FIG. 16A is an illustration of a single wire strand of a prior art stent.

Conventional stents 2 may be formed on an automated knitting machine, using a crochet needle to grip the wire and weave it into the required pattern. The stent 10 illustrated in FIGS. 6-14B may be formed using a manual knitting technique. When the conventional knitted stents are unraveled, the basis of the stent is made up of a single strand 4 of nitinol wire formed in the configuration shown in FIG. 16A. When the stent 10 is unraveled, the stent 10 is made up of a single filament 24 of nitinol wire formed in the configuration shown in FIG. 16B. The difference between the two basic patterns is that the stent 10 pattern contains completed 360° loop portions 30, with a crossed base region 32 in the filament 24, where the wire overlaps itself. The conventional stent, in contrast, includes a series of incomplete loops 3.

Figure 17:
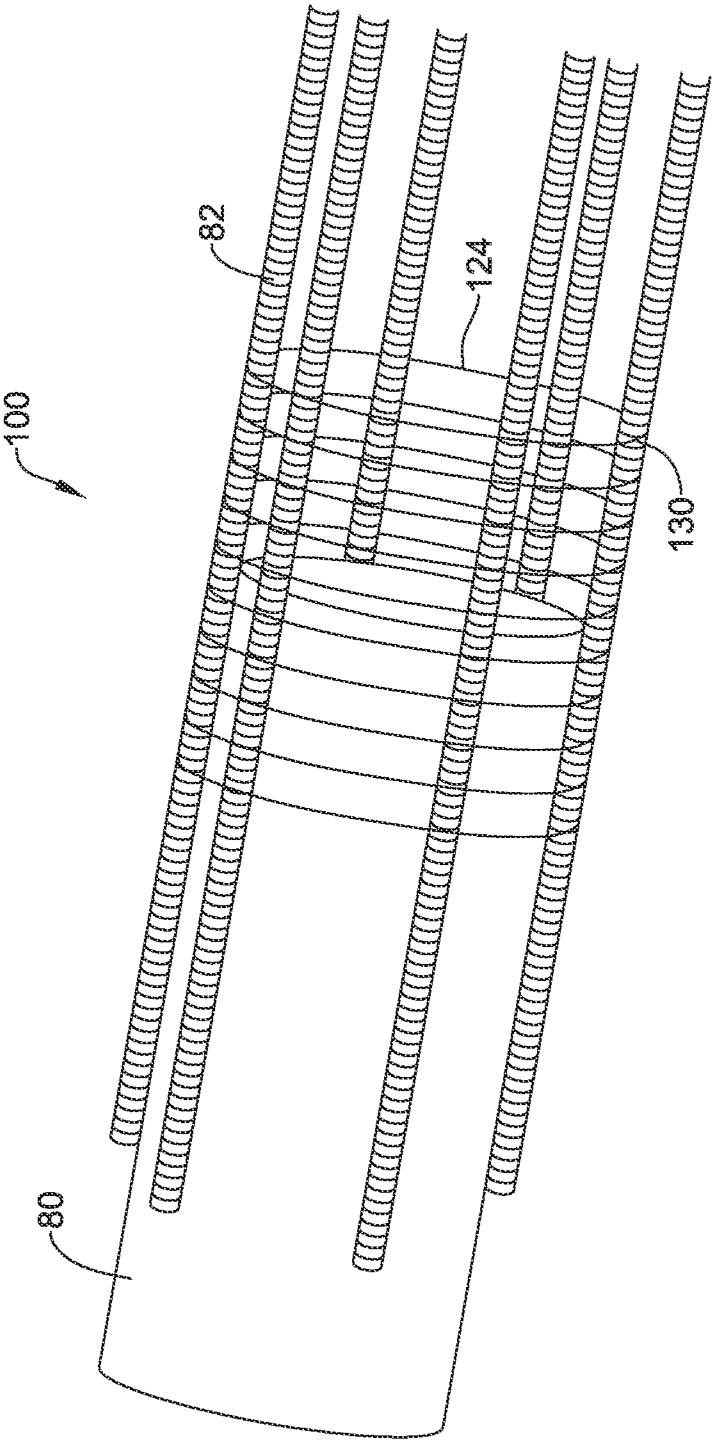
FIG. 17 is a perspective view of an illustrative stent being formed on a mandrel assembly.

FIG. 17 illustrates a perspective view of an illustrative stent 100 being formed about a central mandrel 80. The stent 100 may be similar in form and function to the stent 10 described above. The stent 100 may be formed from a single knitted strand or wire 124. The outer diameter of the central mandrel 80 determines the inner diameter of the stent 10. In addition to the central mandrel 80, multiple threaded mandrels 82 are aligned and attached parallel to the central mandrel 80 at equal degrees of rotation around the central mandrel 80. Differing quantities of threaded mandrels 82 along the circumference of the central mandrel 80 allow for changes in various features and qualities of the stent 10. Altering the quantity and/or diameter of threaded mandrels 82 may change the flexibility and/or conformability of the stent 10 and the hoop force of the stent 10. The diameter of the threaded mandrels 82 determines the diameter of the loops 130 in the expanded configuration, which ultimately determines the space between rungs 26 in the final stent 100. In some examples, the threaded mandrels 82 may have a diameter of between 1 mm and 5 mm. The diameter of the mandrels 82 may be varied along the length of the stent to alter the characteristics of the stent. In some examples, the threaded mandrels 82 may have a larger diameter at the ends, forming a stent 100 with larger diameter loops 130 at the ends. This may result in a stent 100 with increased tissue ingrowth at the ends. In other examples, the threaded mandrels 82 may have a smaller diameter at the ends, forming a stent 100 with increased radial force at the ends to aid the anti-migration properties of the stent. The drainage capabilities of the stent 10 may also be altered to suit the application based on the number of threaded mandrels 82 incorporated.

Figure 18:
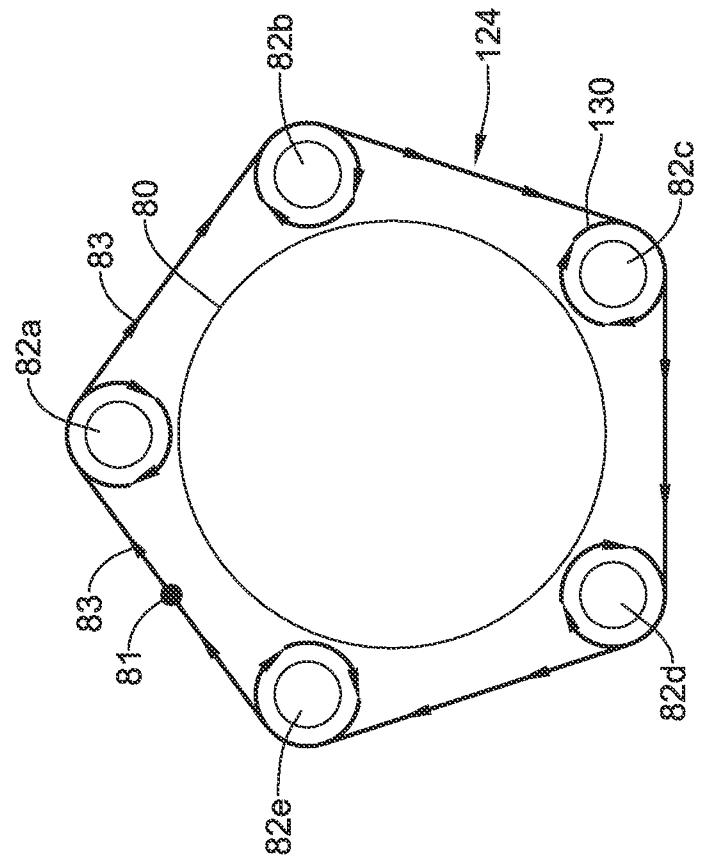
FIG. 18 is an illustration of a method of forming a stent.

Once the threaded mandrels 82 are fixed to the central mandrel 80, the weaving process can begin. The threaded mandrels 82 may be fixed to the central mandrel 80 using any removable fixation method, such as with adhesive tape or wire. The weave is created by wrapping the wire 124 around each individual threaded mandrel 82*a*, 82*b*, 82*c*, 82*d*, 82*e* (collectively 82) around the circumference of the central mandrel 80 as illustrated in FIG. 18. While five threaded mandrels 82 are illustrated in FIG. 18, in other examples, three, four, or more than five threaded mandrels 82 may be used. In general, three to ten threaded mandrels 82 may be used. The number of threaded mandrels 82 and their diameter, along with the diameter of the wire 124 may combine to determine the number and spacing of loops 130 around the circumference of the resulting stent 100. In some examples, between 20 and 80 loops 130 in one circumferential turn of the stent 100. In some specific examples, the stent 100 may have 25, 50, or 60 loops 130 in one circumferential turn.

Figure 16B:
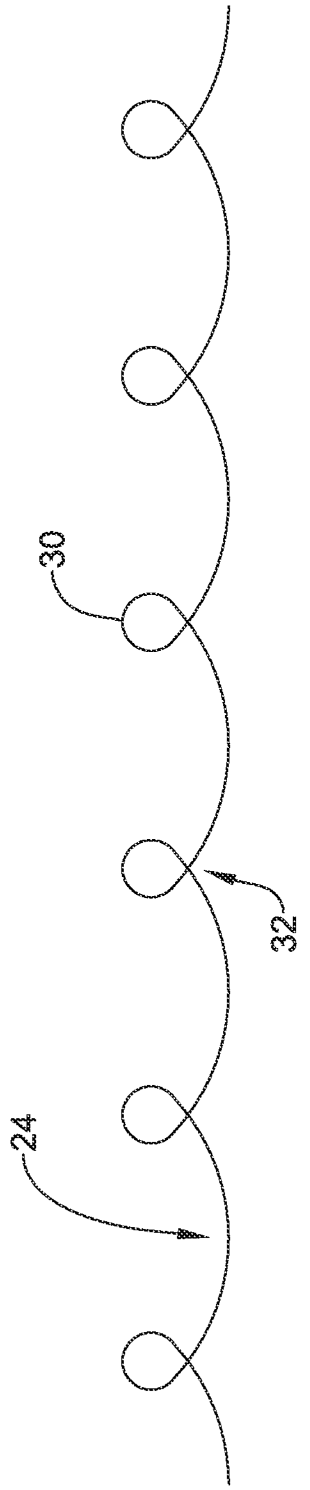
FIG. 16B is an illustration of a single wire strand of the illustrative stent.

The stent 100 may be formed by wrapping in a single direction. For example, in the embodiment illustrated in FIG. 18, the wire 124 is wound in a clockwise direction as shown by arrows 83. However, it should be understood that the stent 100 may be formed by winding in a counterclockwise direction, as desired. The wire 124 may follow a circumferential path around the central mandrel 80 configured to form a plurality of interconnected loops 130. As shown in FIG. 18, from the starting point 81, the wire 124 is wrapped around a first threaded mandrel 82*a*, then across to the second threaded mandrel 82*b*, located circumferentially adjacent the first threaded mandrel 82*a*. Each wrap around a threaded mandrel 82 creates one twisted knit stitch, including the loop portion 30 and crossed base portion 32, as shown in FIG. 16B.

Figure 19:
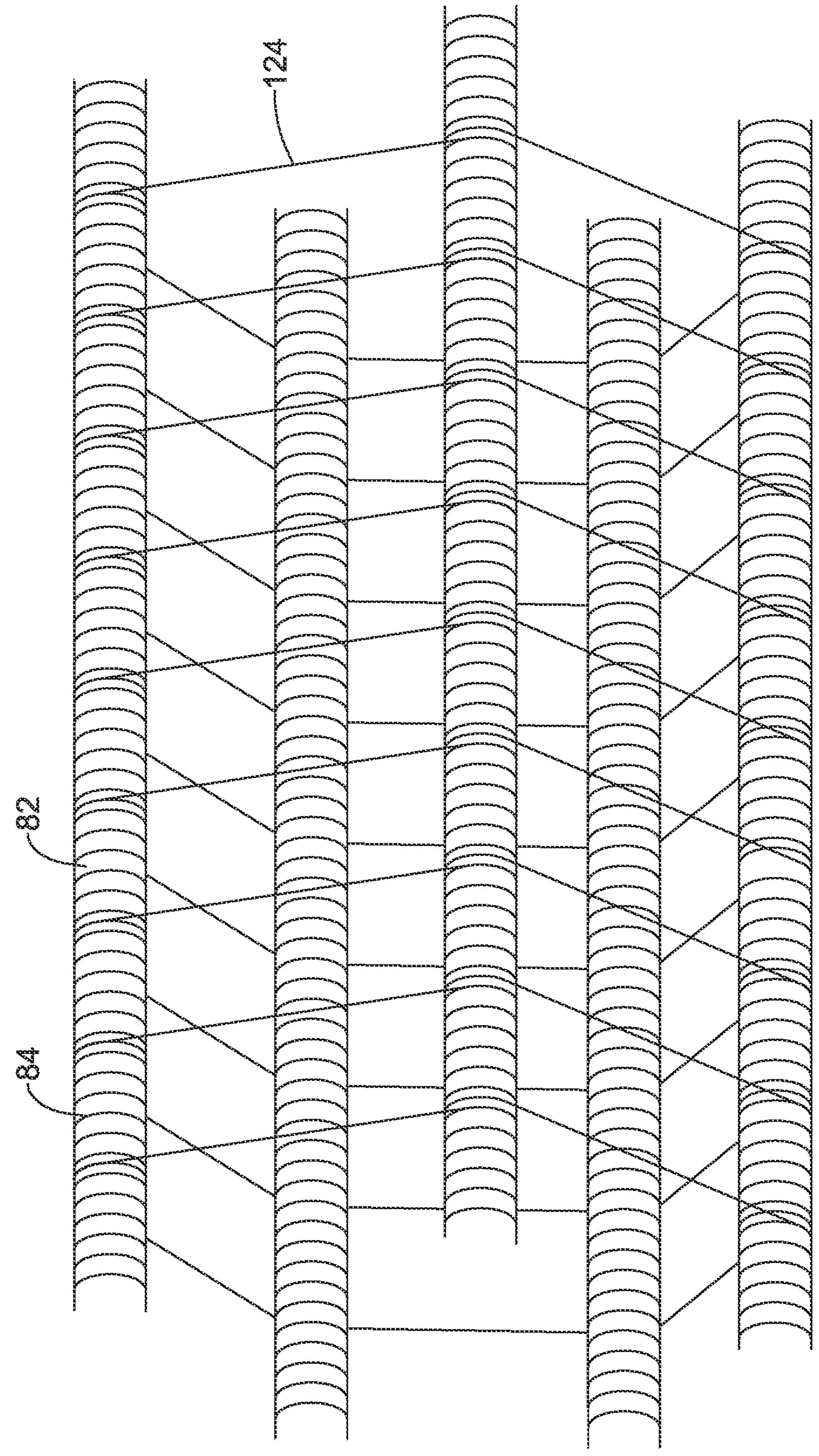
FIG. 19 is a close-up view of a wire strand wound around mandrels.

Once the wire 124 has been wrapped around each threaded mandrel 82*a*, 82*b*, 82*c*, 82*d*, 82*e*, and returns to the starting point 81, the wire is again wrapped around the first threaded mandrel 82*a*, but spaced apart longitudinally from the first wrap. FIG. 19 shows the single wire 124 wrapped around the threaded mandrels 82, with each loop 130 spaced longitudinally along the length of the threaded mandrels 82. The use of a single wire 124 wrapped helically around the threaded mandrels 82 and the central mandrel 80 may create the helical twist of the resulting interconnected loops 130 when the stent 100 is released from the mandrels and moves into the expanded, relaxed configuration shown in FIG. 6. The threaded mandrels 82 may have threading 84 sized to receive the wire 124. In some examples, the threading 84 may have a distance of between 0.1 mm and 1.0 mm between individual threads. In other examples, the distance may be between 0.3 mm and 0.5 mm. The wire 124 may be wrapped with any number of threads left open between longitudinally adjacent loops. Forming the stent 100 with loops closer together longitudinally may create a higher radial force. In some examples, the longitudinal spacing of the loops 130 may be varied along the length of the stent 100. The stent 100 may include as many longitudinal rows of loops 130 as required to form a stent 100 having the desired length. Once the stent 100 has reached the desired length, the wire 124 may be cut and a knot tied in the last loop 130. An adhesive such as a UV glue may be added to the knot to secure it. A similar securement step may be performed on the starting end of the wire 124.

Figure 20:
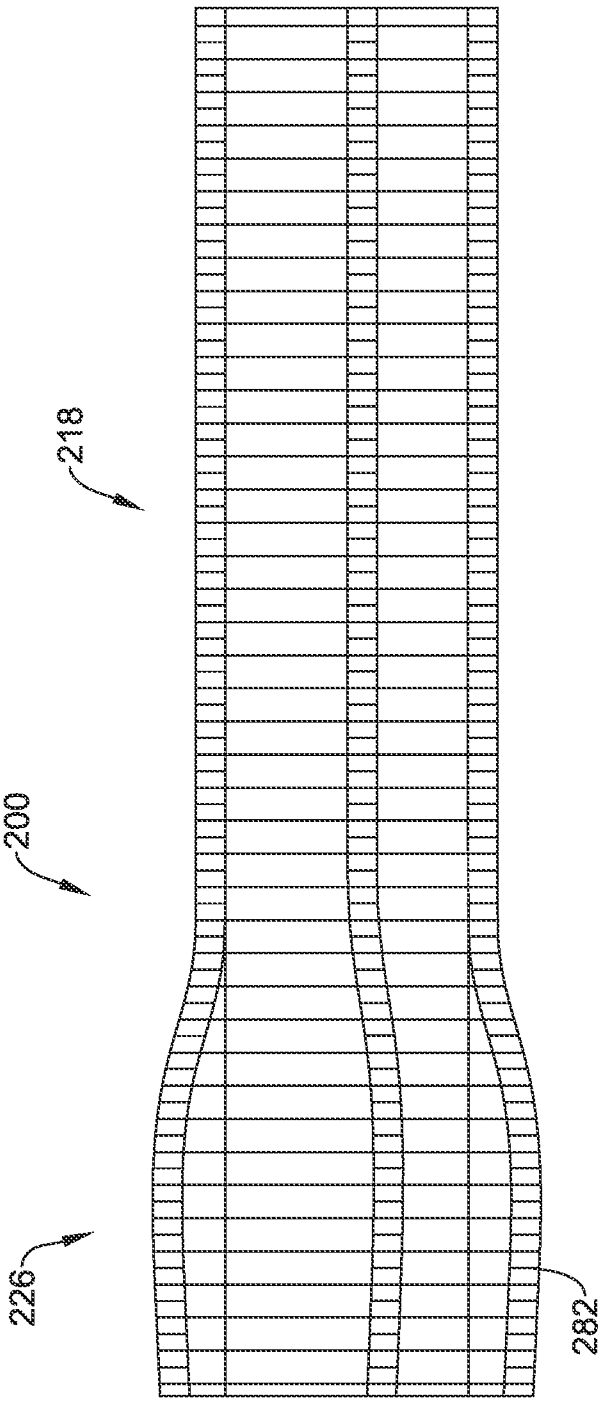
FIG. 20 is a perspective view of a mandrel assembly and stent with a flared end.

The profile of the stent 100 may be modified, to include bumps and hollows, or flares. This may be accomplished by creating a profile on the threaded mandrels 82 prior to weaving. An example of a knitted stent 200 formed with a flared end is shown in FIG. 20. The flare may be created by using threaded mandrels 282 that have been bent such that they define a larger outer diameter at one or both end regions 226 compared to an intermediate region 218.

When the wrapping is complete, the next step of the process involves heat treatment of the wrapped wire at a temperature and time determined by the wire diameter of the weave, material forming the central mandrel 80 (such as aluminum), plus additional processing settings. Once heat set, the nitinol wire maintains the shape, becoming a single strand of wire, with completed loops as seen in FIG. 16B.

Figure 21A:
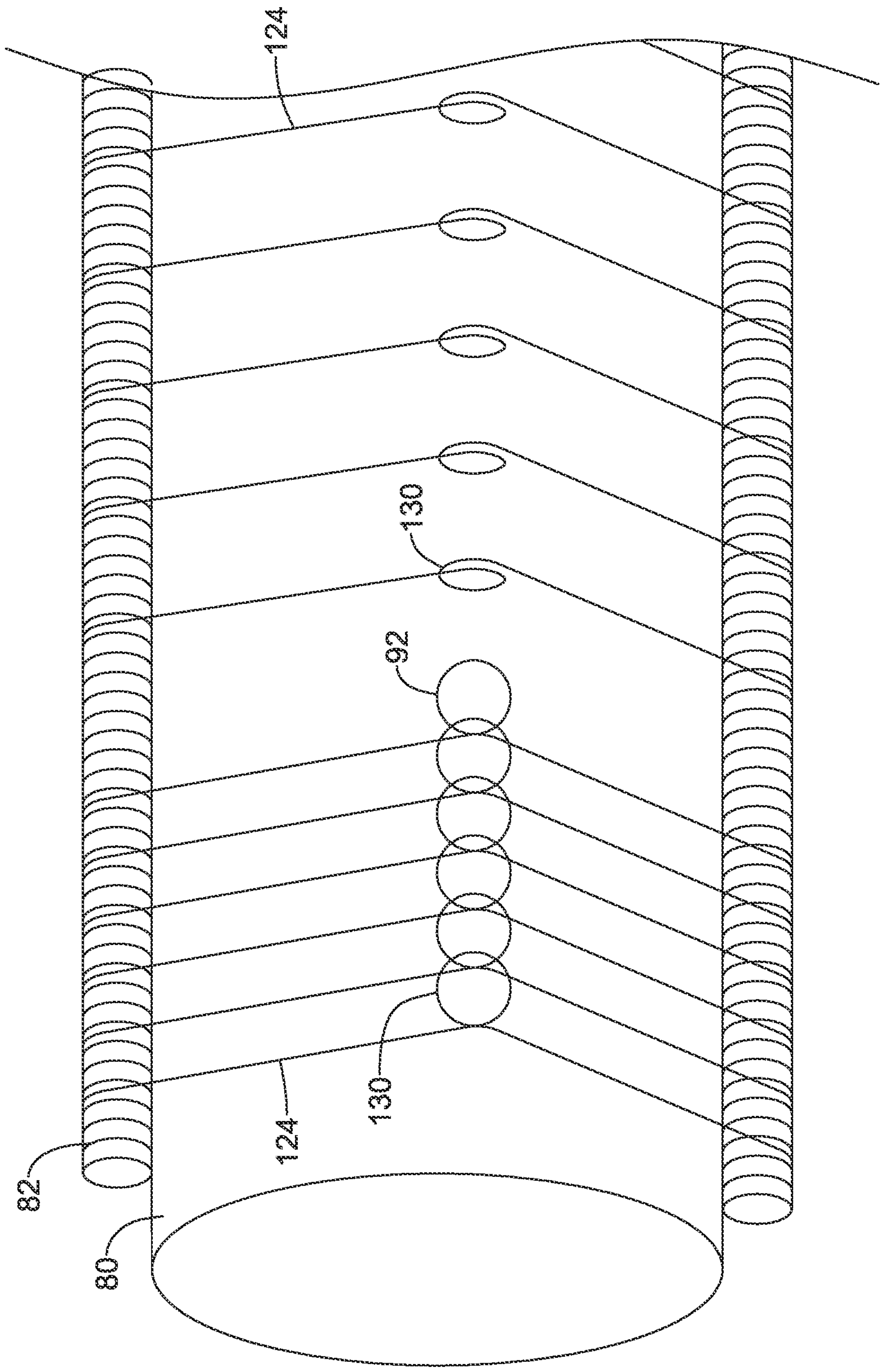
FIGS. 21A and 21B illustrate interconnecting loops to form the illustrative stent.
Figure 21B:
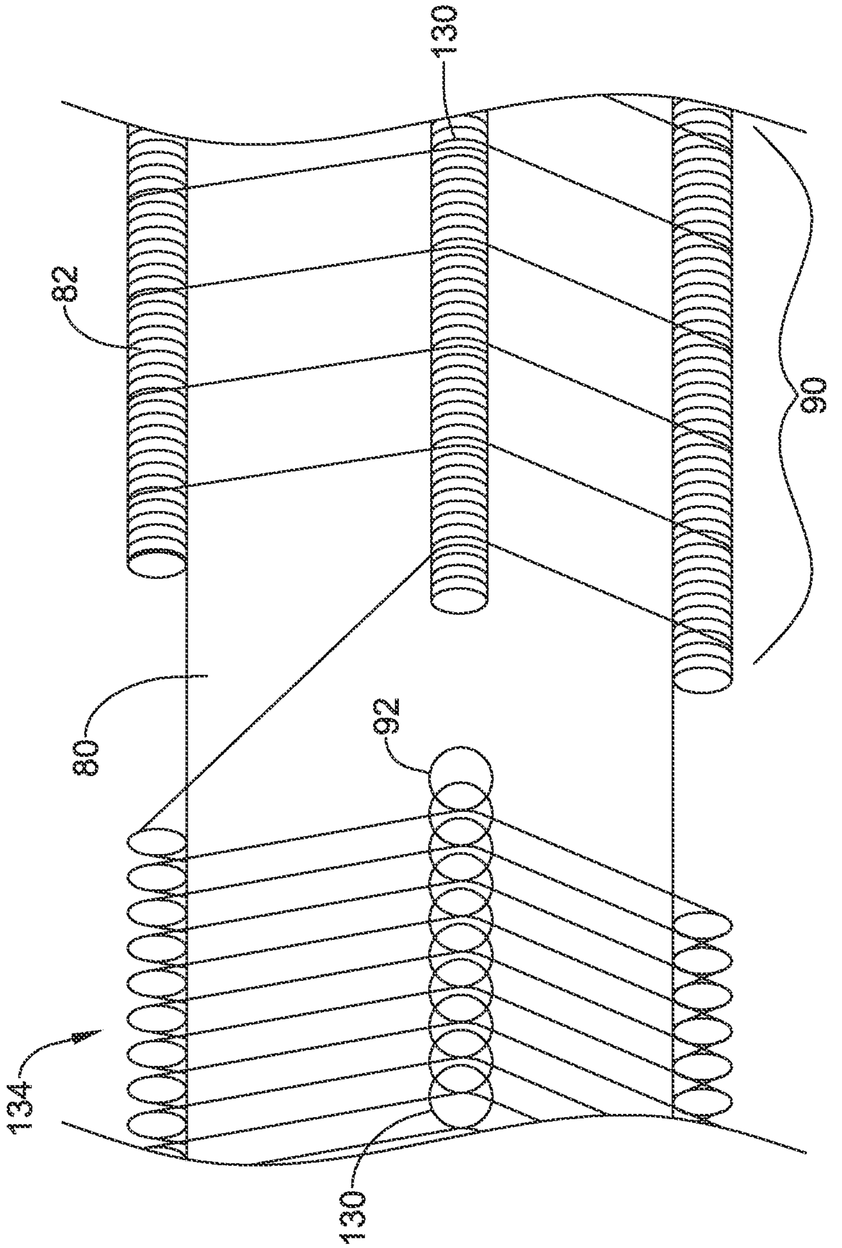

Following heat treatment, removal of the threaded mandrels 82 takes place. At this point, depending on preference, the manufacturer may decide to remove a few the threaded mandrels 82 completely, to sequentially unscrew each threaded mandrel 82 to release a single loop 130, or a combination of both, as can be seen in FIGS. 21A and 21B. The wire 124 maintains the shape set during the heat treatment process. When the threaded mandrels 82 are removed, the loops 130 are maintained in place over the central mandrel 80, as seen in region 90 in FIG. 21B.

Figure 22:
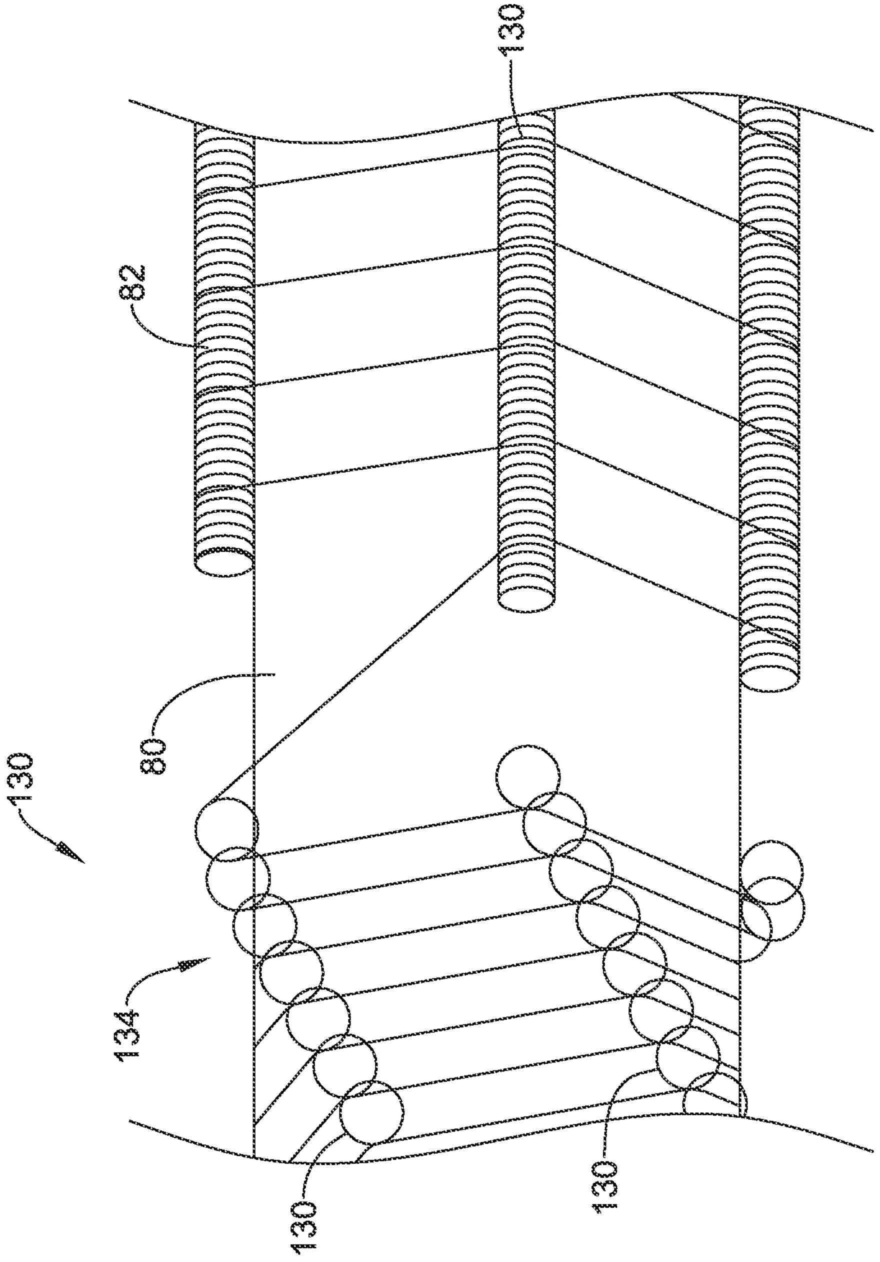
FIG. 22 is a perspective view of the illustrative stent being released from the mandrel assembly.

The next step involves each loop 130 being drawn through the loop 130 on the row above, indicated at arrow 92 in FIGS. 21A and 21B. Once the remaining threaded mandrels 82 are removed from the stent 100, the interconnected loops 130 begin to form helical ridges 134, giving the stent 100 a natural twist into a helical shape as seen in FIGS. 21B and 22. In FIG. 22, some of the threaded mandrels 82 remain within loops 130, keeping the unfinished portion of the stent in a linear configuration.

Changes to the stent design may be created via any (or a combination) of the following process parameters:

- Changing the diameter of the central mandrel 80.
- Changing the pitch and/or diameter of the threaded mandrels 82.
- Changing the number of threaded mandrels 82 around the circumference of the central mandrel 80.
- An irregular spacing of the threaded mandrels 82 around the central mandrel 80.
- Changing the spacing between each loop 130 on the threaded mandrel 82, i.e. every thread, every second thread, etc.
- Changing the diameter of the wire 124.
- Changing the tension on the wire 124 while wrapping.

While the process of forming the stent 100 described above involves manually wrapping the wire 124 and interconnecting the loops 130, it will be understood that this process may be automated. For example, manufacturing of the stent 100 may be automated using tensioned carriers and rotational drives. Further, robotic arms may also be used in combination with rotation drives applied to the threaded mandrels 82 so that the wire 124 may be easily fed through the mandrel assembly in the pattern shown in FIG. 18.

The stents, delivery systems, and the various components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic Nitinol; other nickel alloys such as nickel-chromium-molybdenum alloys, nickel-copper alloys, nickel-cobalt-chromium-molybdenum alloys, nickel-molybdenum alloys, other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys; platinum enriched stainless steel; titanium; combinations thereof; and the like; or any other suitable material.

Some examples of suitable polymers for the stents or delivery systems may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

In at least some embodiments, portions or all of the stents or delivery systems may also be doped with, made of, or otherwise include a radiopaque material. Radiopaque materials are generally understood to be materials which are opaque to RF energy in the wavelength range spanning x-ray to gamma-ray (at thicknesses of <0.005"). These materials are capable of producing a relatively dark image on a fluoroscopy screen relative to the light image that non-radiopaque materials such as tissue produce. This relatively bright image aids the user of the stents or delivery systems in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the stents or delivery systems to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A stent, comprising:

an elongated tubular member having a first end, a second end, and a longitudinal axis extending therebetween, the elongated tubular member formed from at least one filament, the elongated tubular member configured to move between a radially collapsed configuration when constrained and a radially expanded configuration when unconstrained, the elongated tubular member including:

one or more first region in which the at least one filament defines a first knit stitch pattern including a plurality of twisted knit stitches each including a closed loop portion with a crossed base portion in which a portion of the at least one filament forming the closed loop portion crosses over itself, wherein each twisted knit stitch has the crossed base portion in both the radially collapsed configuration and the radially expanded configuration; and one or more second region in which the at least one filament defines a second knit stitch pattern different from the first knit stitch pattern, wherein a longitudinal end of the first region is connected to a longitudinal end of the second region;

wherein the one or more first region and the one or more second region each extends around an entire circumference of the elongated tubular member.

2. The stent of claim 1, wherein the second knit stitch pattern includes a plurality of parallel knit stitches each defined by an incomplete loop having an open base.

3. The stent of claim 1, wherein the plurality of twisted knit stitches forms a series of linked stitches, wherein when in the radially collapsed configuration the series of linked stitches form longitudinal columns of twisted knit stitches and in the radially expanded configuration the series of linked stitches extend helically around the elongated tubular member such that each of the plurality of twisted knit stitches in each series of linked stitches is circumferentially offset from a longitudinally adjacent twisted knit stitch.

4. The stent of claim 1, wherein an entirety of the elongated tubular member is formed by a single filament.

5. The stent of claim 1, wherein a single first region defines the first end of the elongated tubular member and a single second region defines the second end of the elongated tubular member.

6. The stent of claim 5, wherein the single first region and the single second region each define 50% of an overall length of the elongated tubular member.

7. The stent of claim 5, wherein the single first region has a length less than a length of the single second region.

8. The stent of claim 1, wherein the one or more first region includes a proximal first region defining the first end of the elongated tubular member and a distal first region defining the second end of the elongated tubular member, and the one or more second region defines a middle portion of the elongated tubular member disposed between the first end and the second end.

9. The stent of claim 8, wherein the proximal and the distal first regions make up to 25% of an overall length of the elongated tubular member.

10. The stent of claim 1, wherein the closed loop portion of at least some of the twisted knit stitches is wrapped around the crossed base portion of a longitudinally adjacent twisted knit stitch.

11. The stent of claim 3, wherein the at least one filament forms rungs extending circumferentially between radially adjacent twisted knit stitches, wherein when in the radially expanded configuration the rungs define an outer surface of the elongated tubular member and the crossed base portion of each twisted knit stitch extends radially outward from the outer surface.

12. The stent of claim 11, wherein the crossed base portions form a raised ridge extending helically around the elongated tubular member in the radially expanded configuration.

13. The stent of claim 12, wherein the raised ridge has a longitudinal cross-sectional wave shape, with a first slope facing a proximal end of the elongated tubular member, a crest, and a pocket facing a distal end of the elongated tubular member, wherein when inserted within a body lumen, the raised ridge resists distal movement while allowing removal in a proximal direction.

14. A stent, comprising:

an elongated tubular member having a first end, a second end, and a longitudinal axis extending therebetween, an entirety of the elongated tubular member formed from a single filament, the elongated tubular member configured to move between a radially collapsed configuration when constrained and a radially expanded configuration when unconstrained, the elongated tubular member including:

one or more first region in which the filament defines a first knit stitch pattern including a plurality of twisted knit stitches each including a closed loop portion with a crossed base portion in which the filament forming the closed loop portion crosses over itself, wherein each twisted knit stitch has the crossed base portion in both the radially collapsed configuration and the radially expanded configuration; and one or more second region in which the filament defines a second knit stitch pattern including a plurality of parallel knit stitches each defined by an incomplete loop having an open base, wherein a longitudinal end of the first region is directly connected to a longitudinal end of the second region;

wherein the one or more first region and the one or more second region each extends around an entire circumference of the elongated tubular member.

15. The stent of claim 14, wherein a single first region defines the first end of the elongated tubular member and a single second region defines the second end of the elongated tubular member.

16. The stent of claim 14, wherein the one or more first region includes a proximal first region defining the first end of the elongated tubular member and a distal first region defining the second end of the elongated tubular member, and the one or more second region defines a middle portion of the elongated tubular member disposed between the first and the second ends.

17. The stent of claim 14, wherein the plurality of twisted knit stitches forms a series of linked stitches, wherein when in the radially collapsed configuration the series of linked stitches form longitudinal columns of twisted knit stitches and in the radially expanded configuration the series of linked stitches extend helically around the elongated tubular member such that each of the plurality of twisted knit stitches in each series of linked stitches is circumferentially offset from a longitudinally adjacent twisted knit stitch.

18. The stent of claim 17, wherein the at least one filament forms rungs extending circumferentially between radially adjacent twisted knit stitches, wherein when in the radially expanded configuration the rungs define an outer surface of the elongated tubular member and the crossed base portion of each twisted knit stitch extends radially outward from the outer surface.

19. The stent of claim 18, wherein the crossed base portions form a raised ridge extending helically around the elongated tubular member in the radially expanded configuration.

20. A stent, comprising:

an elongated tubular member having a first end, a second end, and a longitudinal axis extending therebetween, the elongated tubular member formed from at least one filament, the elongated tubular member including:

one or more first region in which the at least one filament defines a first knit stitch pattern including a plurality of twisted knit stitches each including a closed loop portion with a crossed base portion in which a portion of the at least one filament forming the closed loop portion crosses over itself; and one or more second region in which the at least one filament defines a second knit stitch pattern including a plurality of parallel knit stitches each defined by an incomplete loop having an open base, wherein a longitudinal end of the first region is connected to a longitudinal end of the second region;

wherein the plurality of twisted knit stitches forms a series of linked stitches, wherein the elongated tubular member is configured to move between a radially collapsed configuration when constrained and a radially expanded configuration when unconstrained, wherein when in the radially collapsed configuration the series of linked stitches form longitudinal columns of twisted knit stitches and in the radially expanded configuration the series of linked stitches extend helically around the elongated tubular member such that each of the plurality of twisted knit stitches in each series of linked stitches is circumferentially offset from a longitudinally adjacent twisted knit stitch;

wherein each twisted knit stitch has the crossed base portion in both the radially collapsed configuration and the radially expanded configuration;

wherein the one or more first region and the one or more second region each extends around an entire circumference of the elongated tubular member.

* * * * *